US012673094B2

(12) United States Patent
Wilmes et al.

(10) Patent No.: US 12,673,094 B2
(45) **Date of Patent: \*Jul. 7, 2026**

(54) METHOD OF PRODUCING AN IMMUNOGENIC COMPOSITION

(71) Applicant: Boehringer Ingelheim Animal Health USA Inc., Duluth, GA (US)

(72) Inventors: Leigh Wilmes, Oregon, MO (US); Matthew Coons, Dearborn, MO (US); Amanda Brown, St. Joseph, MO (US); Michael Johannes Gassel, Ingelheim am Rhein (DE); Francois-Xavier Orveillon, Shanghai (CN); Katharina Hedwig Toepfer, Hannover (DE); Elida Bautista, St. Joseph, MO (US); Kathy Schlesinger, St. Joseph, MO (US)

(73) Assignee: Boehringer Ingelheim Animal Health USA Inc., Duluth, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/615,838

(22) Filed: Mar. 25, 2024

(65) Prior Publication Data

US 2024/0350612 A1 Oct. 24, 2024

Related U.S. Application Data

(63) Continuation of application No. 16/980,785, filed as application No. PCT/US2019/023932 on Mar. 25, 2019, now Pat. No. 11,957,746.

(30) Foreign Application Priority Data

Mar. 26, 2018 (EP) ..................................... 18163918

(51) Int. Cl.
*A61K 39/12* (2006.01)
*A61K 39/00* (2006.01)
(Continued)

(52) U.S. Cl.
CPC .............. *A61K 39/12* (2013.01); *A61P 31/20* (2018.01); *C12N 15/86* (2013.01);
(Continued)

(58) Field of Classification Search
None
See application file for complete search history.

(56) References Cited

U.S. PATENT DOCUMENTS 9,561,270 B2 * 2/2017 Kohler .................... A61P 31/12
11,957,746 B2 * 4/2024 Wilmes .................. A61P 31/20
(Continued)

FOREIGN PATENT DOCUMENTS

CN 102573899 A 7/2012
EP 0366239 A1 5/1990
(Continued)

OTHER PUBLICATIONS

Wang Yahua "Veterinary Biological Product Technology" China Agricultural University Press, 2009, pp. 103.
(Continued)

*Primary Examiner* — Shanon A. Foley
(74) *Attorney, Agent, or Firm* — Suzanne Seavello Shope

(57) ABSTRACT

The present invention in particular relates to a method of producing an immunogenic composition exhibiting reduced virucidal activity, as well as to the immunogenic composition and uses thereof, wherein the method in particular comprises the steps of: (a) providing a mixture with a first liquid and a recombinant protein, (b) concentrating the recombinant protein in the mixture by removing a portion of the first liquid from the mixture, and (c) processing the solution resulting from step (b) by continuous diafiltration.

23 Claims, 1 Drawing Sheet
Specification includes a Sequence Listing.

(51) Int. Cl.
  *A61P 31/20*    (2006.01)
  *C12N 15/86*    (2006.01)
(52) U.S. Cl.
  CPC .................. *A61K 2039/523* (2013.01); *A61K 2039/5252* (2013.01); *A61K 2039/5256* (2013.01); *A61K 2039/5258* (2013.01); *C12N 2710/14034* (2013.01); *C12N 2710/14042* (2013.01); *C12N 2710/14062* (2013.01)

(56)     References Cited

U.S. PATENT DOCUMENTS

| | | |
|---|---|---|
| 2005/0186221 A1 | 8/2005 | Reynolds et al. |
| 2011/0059126 A1 | 3/2011 | Kohler et al. |

FOREIGN PATENT DOCUMENTS

| | | | |
|---|---|---|---|
| EP | 2460818 A2 | 6/2012 |
| JP | H03130082 A | 6/1991 |
| JP | 2013503893 A | 2/2013 |
| JP | 2016531859 A | 10/2016 |
| JP | 2017506643 A | 3/2017 |
| WO | 2006072065 A2 | 7/2006 |
| WO | 2008081015 A1 | 7/2008 |
| WO | 2011028888 A2 | 3/2011 |
| WO | 2012051147 A1 | 4/2012 |
| WO | 2013009491 A2 | 1/2013 |
| WO | 2013152086 A1 | 10/2013 |
| WO | 2015044337 A2 | 4/2015 |
| WO | 2015124594 A1 | 8/2015 |
| WO | 2017051273 A1 | 3/2017 |
| WO | 2017109225 A1 | 6/2017 |
| WO | 2018033482 A1 | 2/2018 |
| WO | 2018083156 A1 | 5/2018 |

OTHER PUBLICATIONS

Jin Yu et al., Complete Book on Modern biopharmaceutical Process Technology, Quality Monitoring, New Drug Development and Pharmaceutical Equipment Practice, first edition, Contemporary China audio-visual publishing house, 2004, pp. 1240-1241.

Tang Qiuyan et al. "Practical technology of immunodiagnostic reagents" China Ocean Press, 2009, pp. 45-46.

Annex I Summary of Product Characteristics: Ingelvac CircoFLEX suspensions for injections for pigs; EPAR product information; European Medical Agency, Feb. 13, 2008, Retrieved from the Internet: URL:http://www.ema.europa.eu/docs/en_GB/document_library/EPAR-Product_Information/veterinary/000126/WC500062388.pdf [retrieved on Jan. 29, 2015].

Schaepertoens, Marc et al., "Solvent recycle with imperfect membranes: A semi-continuous workaround for diafiltration", Journal of Membrane Science, Elsevier BV, Apr. 26, 2016, vol. 514, pp. 646-658, XP029611897.

Alignment of SEQ 1 with Geneseq db access AZF69095 by Kohler et al. 2011.

Liu Gang, et al. "Dietary L-arginine supplementation improves the immune responses in mouse model infected porcine circovirus types 2." J Anim Vet Adv 11 (2012): 2980-5.

Rueda et al. (Vaccine. 2001; 19: 726-73).

Zanotti et al. (Biologicals. 2015; 43: 79-83).

Xi Jun Chai, et al. "The purification of Recombinant Hepatitis B Surface Antigen by Hollow Fibre Ultrafiltration Membrane Diafiltration" Springer link published on Jul. 1992_ vol. 6_ No. 4_p. 281_384, found via web link https://link.springer.com/article /10.1007/BF02439330_ Mar. 1, 2014.

* cited by examiner

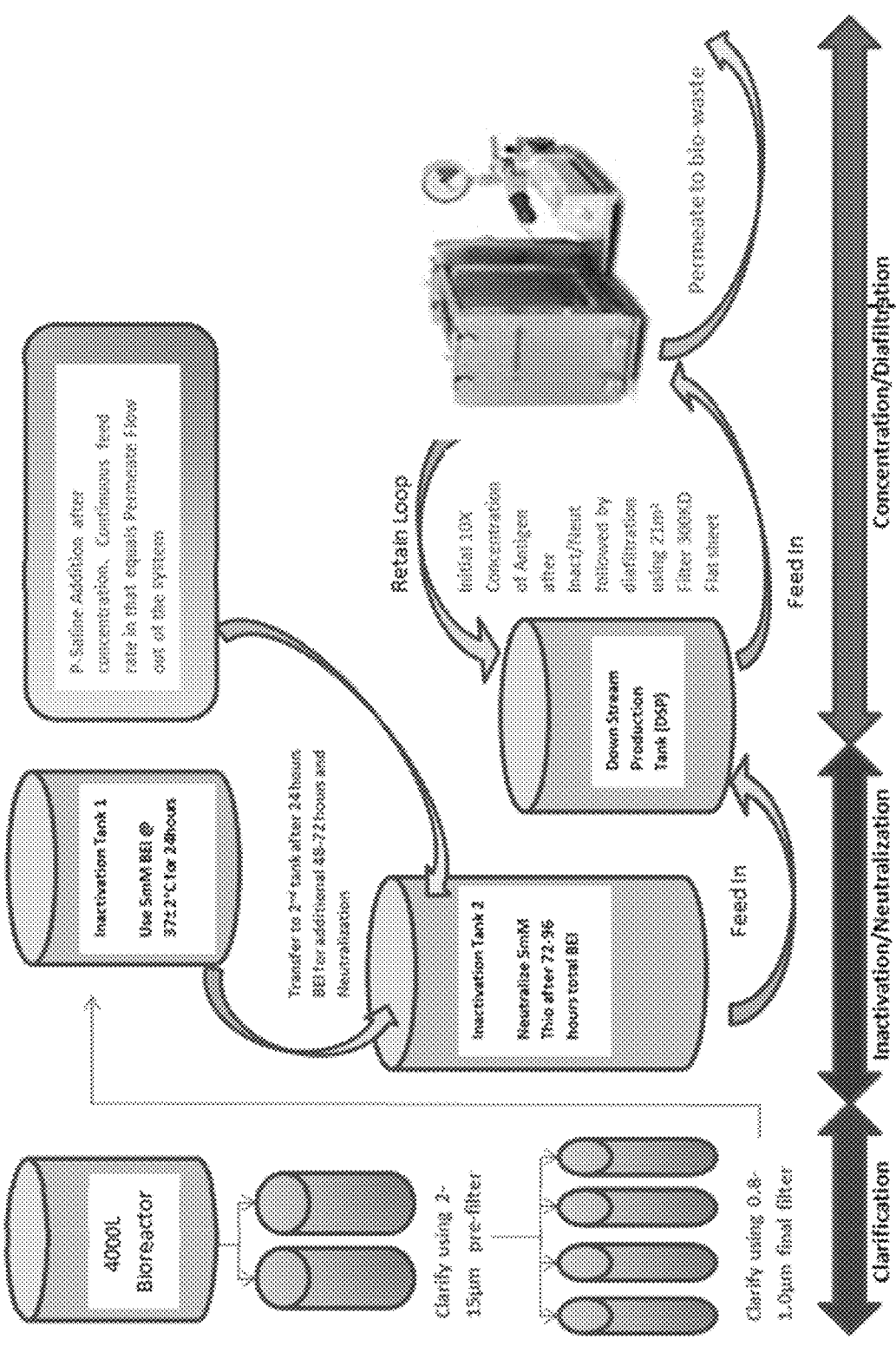

METHOD OF PRODUCING AN IMMUNOGENIC COMPOSITION

CROSS-REFERENCE TO RELATED APPLICATIONS

This application is a continuation of U.S. patent application Ser. No. 16/980,785, filed Sep. 14, 2020, which claims the benefit of International Application No. PCT/US2019/023932, filed Mar. 25, 2019, which claims the benefit of European Application No. 18163918.8, filed Mar. 26, 2018, the entire contents of which are hereby incorporated by reference herein.

SEQUENCE LISTING

The instant application contains a Sequence Listing which has been submitted electronically in XML file format and is hereby incorporated by reference in its entirety. Said XML copy, created on Mar. 5, 2024, is named 10-0180-US-1_SL.xml and is 3,397 bytes in size.

BACKGROUND OF THE INVENTION

Technical Field

The present invention relates to methods of producing immunogenic compositions as well as such immunogenic compositions exhibiting reduced virucidal activity.

Background Information

Porcine circovirus type 2 (PCV2) is a small (17-22 nm in diameter), icosahedral, non-enveloped DNA virus, which contains a single-stranded circular genome. PCV2 shares approximately 80% sequence identity with porcine circovirus type 1 (PCV1). However, in contrast with PCV1, which is generally non-virulent, swine infected with PCV2 exhibit a syndrome commonly referred to as Post-weaning Multisystemic Wasting Syndrome (PMWS). PMWS is clinically characterized by wasting, paleness of the skin, unthriftiness, respiratory distress, diarrhea, icterus, and jaundice. In some affected swine, a combination of all symptoms will be apparent while other swine will only have one or two of these symptoms. During necropsy, microscopic and macroscopic lesions also appear on multiple tissues and organs, with lymphoid organs being the most common site for lesions. A strong correlation has been observed between the amount of PCV2 nucleic acid or antigen and the severity of microscopic lymphoid lesions. Mortality rates for swine infected with PCV2 can approach 80%. In addition to PMWS, PCV2 has been associated with several other infections including pseudorabies, porcine reproductive and respiratory syndrome (PRRS), Glasser's disease, streptococcal meningitis, *salmonellosis*, postweaning colibacillosis, dietetic hepatosis, and suppurative bronchopneumonia.

Several vaccines are available to reduce the impact of PCV2 infections in pigs. U.S. Pat. No. 6,703,023 provides a DNA based vaccine for the prophylaxis of pigs against PMWS. In WO 03/049703 production of a live chimeric vaccine is described, comprising the non-pathogenic PCV1 virus in which, however, the ORF2 protein is replaced by the ORF2 protein of the pathogenic PCV2. WO 99/18214 and WO 99/29717 have provided several PCV2 strains and procedures for the preparation of a killed PVC2 vaccine. Preparation of subunit vaccines have also been described in WO 99/18214 and WO 99/29717. An effective ORF2 based subunit vaccine has been reported in WO 06/072065. A further ORF2 based subunit vaccine is described also in WO 07/28823.

Open reading frame 2 (ORF2) protein of PCV2, having an approximate molecular weight of 30 kDa when run on SDS-PAGE gel, has been utilized in the past as an antigenic component in vaccines and immunogenic compositions for PCV2. Typical methods of obtaining ORF2 for use in such vaccines and compositions generally consist of amplifying the PCV2 DNA coding for ORF2, expressing the ORF2 protein within a host cell, and extracting the ORF2 protein from the host cell via cell lysis. The recovered ORF2 cell lysate is then used as the antigenic portion of an immunogenic composition or vaccine. In some cases the ORF2 containing cell lysate is separated from the cell debris.

Immunogenic compositions against PCV2 and various immunogenic compositions against other pathogens often have a virucidal effect on other antigens. For instance, current regulatory standards in the U.S. (9 CFR 113.35) permit some virucidal activity in multivalent compositions, but this virucidal activity cannot result in a loss of more than 0.7 logs/mL of a live virus or less than 0.7 logs/mL CFU of live bacteria when combined with the other components of the immunogenic composition. Compositions that have more virucidal activity than permitted cannot be combined with other antigens to create a multivalent vaccine.

To this end, WO 11/28888 provides methods of reducing the virucidal activity of a composition comprising a PCV2 antigen as well as antigenic preparations and immunogenic compositions comprising a PCV2 antigen, wherein the virucidal activity has been reduced. More particular, WO 11/28888 teaches a method of producing such a PCV2 antigenic composition in a large scale, wherein the method comprises the steps of:

i) obtaining a first liquid containing therein PCV2 antigen comprising virus like particles of ORF2 protein; and ii) removing at least a portion of the first liquid from the PCV2 antigen comprising virus like particles of ORF2 protein by a filtration step utilizing a filter, wherein the filter includes a semi-permeable membrane having an average pore size that is smaller than the PCV-2 antigen to thereby prevent passage of at least 90% of the PCV2 antigen through the semipermeable membrane pores and hold the PCV2 antigen within the filter, wherein the portion of the first liquid is removed from the PCV2 antigen by an exchange of the portion of the first liquid against a second liquid, wherein the second liquid is different from the first liquid, and wherein the exchange of the portion of the first liquid with the second liquid comprises the steps of:

a) liquid addition comprising adding the second liquid to the first liquid which contains the PCV-2 antigen; and b) concentrating the PCV-2 antigen from 3× to 50× in comparison to the volume of the first liquid by removing a portion of the first and second liquids.

However, said liquid addition step a), comprising adding the second liquid preferably in an excess volume to the first liquid, may result in a limitation regarding the volume of the total production scale, as the resulting volume of the first and second liquid is usually increased by a multiple, before the concentration step b), as compared to the volume of the first liquid.

Thus, further methods are desired to produce immunogenic compositions comprising a recombinant protein with reduced virucidal effect in a still larger scale and even in a very large scale.

DESCRIPTION OF THE INVENTION

The solution to the above technical problems is achieved by the description and the embodiments characterized in the claims.

Thus, the invention in its different aspects is implemented according to the claims.

The invention is based on the surprising finding that a method of producing an immunogenic composition comprising a recombinant protein is sufficient for the desired purposes, wherein the method consists of or comprises the steps, preferably in the following order, of:

(a) providing a mixture containing a first liquid, and recombinant protein and/or quaternary structures comprising a plurality of said recombinant protein, (b) concentrating the recombinant protein and/or said quaternary structures in the mixture resulting from step (a) by removing a portion of the first liquid from the mixture, and (c) processing the solution resulting from step (b) by continuous diafiltration, in particular by continuous diafiltration against a second liquid, wherein the second liquid is different from the first liquid.

It is understood that the term "first liquid", as used herein, is equivalent to the term "initial liquid" or "liquid (1)", respectively. Thus, the term "first liquid" is interchangeable with the term "liquid (1)" or with the term "initial liquid".

It is further understood that the term "second liquid", as used herein, is equivalent to the term "further liquid" or "liquid (2)", respectively. Thus, the term "second liquid" is interchangeable with the term "liquid (2)" or with the term "further liquid".

In one preferred aspect, the mixture of step (a) additionally contains a vector comprising a nucleic acid sequence encoding said recombinant protein, wherein said vector has been inactivated by an inactivating agent. According to another preferred aspect, the mixture of step (a) additionally contains an inactivating agent, which has been neutralized by a neutralizing agent.

In yet another preferred aspect, the mixture of step (a) additionally contains a neutralizing agent.

As mentioned herein, it is in particular understood that the term "mixture of step (a)" is synonymous with "mixture provided in step (a)". The term "provided in step", as used herein, is in particular understood to be equivalent to "provided by step".

The present invention further relates to the method as herein described and/or claimed, wherein the mixture of step (a) supra additionally contains a vector comprising a nucleic acid sequence encoding said recombinant protein, wherein said vector has been inactivated by an inactivating agent, and/or an inactivating agent, which has been neutralized by a neutralizing agent, and/or a neutralizing agent, and wherein preferably the mixture of step (a) additionally contains said vector, said neutralized inactivating agent and the neutralizing agent.

Furthermore, in step (c) the solution resulting from step (b) is preferably processed by continuous diafiltration such that the concentration of the neutralized inactivating agent and/or the concentration of the neutralizing agent is decreased in the process solution.

Before the aspects of the present invention are described, it must be noted that as used herein and in the appended claims, the singular forms "a", "an", and "the" include plural reference unless the context clearly dictates otherwise. Thus, for example, reference to "an antigen" includes a plurality of antigens, reference to the "virus" is a reference to one or more viruses and equivalents thereof known to those skilled in the art, and so forth. Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies as reported in the publications which might be used in connection with the invention. Nothing herein is to be construed as an admission that the invention is not entitled to antedate such disclosure by virtue of prior invention.

In one aspect, the present invention concerns a method of producing an immunogenic composition comprising a recombinant protein, wherein the method consists of or comprises the steps, preferably in the following order, of:

(a)(i) providing a mixture containing a first liquid, recombinant protein and/or quaternary structures comprising a plurality of said recombinant protein, and a vector comprising a nucleic acid sequence encoding said recombinant protein;

(ii) inactivating the vector by adding an inactivating agent to the mixture of step (i);

(iii) neutralizing the inactivating agent by adding a neutralizing agent to the mixture resulting from step (ii);

(b) concentrating the recombinant protein and/or said quaternary structures in the mixture resulting from step (a)(iii) by removing a portion of the first liquid from the mixture, (c) and processing the solution resulting from step (b) by continuous diafiltration such that the concentration of the neutralized inactivating agent and/or the concentration of the neutralizing agent is decreased in the process solution.

In particular, the continuous diafiltration of step (c) is a continuous diafiltration against a second liquid, wherein the second liquid is different from the first liquid.

In the context of the present invention it is in particular understood that "(i)", "(ii)" and "(iii)" denote sub-steps of step (a) or, respectively, step (a) consists of or comprises the sub-steps "(i)", "(ii)" and "(iii)", and that thus "(i)" is equivalent to "(a)(i)", "(ii)" is equivalent to "(a)(ii)" and "(iii)" is equivalent to "(a)(iii)".

As mentioned herein, it is in particular understood that the term "mixture of step (i)" and "mixture of step (a)(i)", respectively, is synonymous with "mixture provided in step (i)" and "mixture provided in step (a)(i)", respectively.

For purposes of the present invention, a "first liquid" refers to liquid, aqueous, or fluid media typically used in combination with cells, antigens, immunogenic compositions, vaccines, and the like. Preferably, the first liquid comprises media from an antigenic composition; more preferably, the first liquid comprises or preferably consists of cell culture media used for the production of recombinant proteins in cultivated host cells. Said cultivated host cells can be bacteria, yeasts, insect cells, animal cells, and mammalian cells, with insect and mammalian cells being particularly preferred. Thus, the first liquid may comprise or consist of media for the cultivation of bacteria, yeast, insect cells, animal cells or mammalian cells. Preferably, the cell media is serum free cell media, and most preferably the culture media is Excell 420 serum free media, when insect cells are used.

In another aspect, the present invention thus concerns a method as herein described and claimed, wherein said first liquid comprises a portion of cell culture medium or consists of cell culture medium, and wherein the cell culture medium is preferably insect cell culture medium.

"Portion", for purposes of the present invention, refers to any amount which does not encompass the entire amount. For example, a portion of liquid would be anything less than 100% of the volume of the liquid, such as 90% of the liquid, 80% of the liquid, 70% of the liquid, and all amounts between more than 0% and less than 100%.

The term "recombinant protein", as used herein, in particular refers to a protein which is produced by recombinant DNA techniques, wherein generally DNA encoding the expressed protein is inserted into a suitable expression vector which is in turn used to transform or, in the case of a virus vector, to infect a host cell to produce the heterologous protein. Thus, the term "recombinant protein", as used herein, particularly refers to a protein molecule that is expressed from a recombinant DNA molecule. "Recombinant DNA molecule" as used herein refers to a DNA molecule that is comprised of segments of DNA joined together by means of molecular biological techniques. Suitable systems for production of recombinant proteins include but are not limited to insect cells (e.g., baculovirus), prokaryotic systems (e.g., *Escherichia coli*), yeast (e.g., *Saccaromyces cerevisiae, Pichia pastoris*), mammalian cells (e.g., Chinese hamster ovary, HEK293), plants (e.g., safflower), avian cells, amphibian cells, fish cells, and cell-free systems (e.g., rabbit reticulocyte lysate).

In the context of the present invention a recombinant protein is preferably a recombinant PCV2 ORF2 protein.

The term "quaternary structure" as used in the context of the present invention in particular relates to the assembly of multiple folded protein molecules in a multi-subunit complex, and in particular relates to a virus-like particle.

A "quaternary structure comprising a plurality of said recombinant protein", for purposes of the present invention, refers to a three-dimensional arrangement of a plurality of said recombinant protein, such as a virus-like particle comprising a plurality of said recombinant protein. In this regard, it is in particular understood that the term "plurality of said recombinant protein" is equivalent to "plurality of a recombinant protein". It is particularly understood that said term means a virus-like particle comprising several molecules of a particular recombinant protein, e.g. of a recombinant PCV2 ORF2 protein. "Inactivating the vector", in the context of the present invention, in particular means that the vector, normally capable of replication, is rendered unable to replicate. "Inactivation" in particular refers to the process of inactivating a vector.

"Inactivating agent", for purposes of the present invention, refers to any agent that can be used in any conventional inactivation method. Inactivation can be performed by chemical and/or physical treatments which are known to the person skilled in the art. Preferred inactivating agents include cyclized binary ethylenimine (BEI) including a solution of 2-bromoethyleneamine hydrobromide (BEA), which has been cyclized to binary ethylenimine (BEI). Preferred further chemical inactivation agents comprise but are not limited to Triton X-100, Sodium deoxycholate, Cetyltrimethylammonium bromide, β-Propiolactone, Thimerosal, Phenol and Formaldehyde (Formalin). The term "inactivating agent", as used herein, thus in particular relates to a chemical agent capable of modifying a vector by chemical reaction such that the vector is rendered unable to replicate.

Preferably, the inactivating agent is an aziridine compound, in particular binary ethylenimine (BEI) and/or the inactivating agent is added in a molar excess in relation to the vector, and in particular in a molar excess in relation to the nitrogenous bases of the vector DNA base pairs reacting with BEI.

"Neutralizing agent", for purposes of the present invention, refers to any agent capable of neutralizing the inactivating agents as herein described such that the inactivating agent is no longer capable of inactivating a vector. If an aziridine compound is used for the inactivation, then preferably a nucleophile which opens the three-membered ring is used for the neutralization. The agent that neutralizes the inactivating agent is preferably sodium thiosulfate, sodium bisulfite and the like.

It is in particular preferred that the neutralizing agent is sodium thiosulfate and/or that the neutralizing agent is added in a molar excess in relation to the inactivating agent.

"Neutralized inactivating agent", as described herein, in particular relates to the product or the products resulting from the chemical reaction of the inactivating agent with the neutralizing agent, e.g. to the products of the chemical reaction of BEI with thiosulfate or an other nucleophile.

Any conventional chemical inactivation method can be used for inactivating the vector. In preferred forms, for the chemical treatment, the temperature is brought to between about 32° C.-42° C., more preferably between about 34° C.-40° C., and most preferably between about 35° C.-39° C. Preferred inactivation methods include the addition of cyclized binary ethylenimine (BEI), preferably in a concentration of about 1 to about 20 mM, preferably of about 2 to about 10 mM, still more preferably of about 2 to about 8 mM, still more preferably of about 3 to about 7 mM, most preferably of about 5 mM. For example the inactivation includes the addition of a solution of 2-bromoethyleneamine hydrobromide (BEA), preferably of about 0.4 M, which has been cyclized to 0.2 M binary ethylenimine (BEI) in 0.3 N NaOH, to the fluids to give a final concentration of about 5 mM BEI. Preferably, the fluids are then stirred continuously for 2-96 hours. After inactivation is completed a sodium thiosulfate solution, preferably at 1.0 M is added to neutralize any residual BEI, and the inactivated/neutralized harvest fluids can be stored frozen at −40° C. or below or between about 1° C.-7° C. Preferably, the sodium thiosulfate is added in equivalent amount as compared to the BEI added prior to for inactivation. For example, in the event BEI is added to a final concentration of 5 mM, a 1.0 M sodium thiosulfate solution is added to give a final minimum concentration of 5 mM to neutralize any residual BEI.

Thus, in step (iii) the neutralizing agent is preferably added in an equivalent amount as compared to the amount of inactivating agent added in step (ii). In the context of ranges, as described herein, it is in particular understood that "y-z" is equivalent to "y-z", and both are equivalent to "y to z", respectively, such that, for instance, "0.1-1.0" is equivalent to "0.1-1.0".

"Vector" as well as "vector comprising a nucleic acid sequence encoding said recombinant protein", for purposes of the present invention, refers to a suitable expression vector, preferably a baculovirus expression vector, which is in turn used to transfect, or in case of a baculovirus expression vector to infect, a host cell to produce the protein or polypeptide encoded by the DNA. Vectors and methods for making and/or using vectors (or recombinants) for expression can be made or done by or analogous to the methods disclosed in: U.S. Pat. Nos. 4,603,112, 4,769,330, 5,174, 993, 5,505,941, 5,338,683, 5,494,807, 4,722,848, 5,942,235, 5,364,773, 5,762,938, 5,770,212, 5,942,235, 382,425, PCT publications WO 94/16716, WO 96/39491, WO 95/30018; Paoletti, "Applications of pox virus vectors to vaccination: An update, "PNAS USA 93:11349-11353, October 1996; Moss, "Genetically engineered poxviruses for recombinant gene expression, vaccination, and safety," PNAS USA 93:11341-11348, October 1996; Smith et al., U.S. Pat. No. 4,745,051 (recombinant baculovirus); Richardson, C. D. (Editor), Methods in Molecular Biology 39, "Baculovirus Expression Protocols" (1995 Humana Press Inc.); Smith et al., "Production of Human Beta Interferon in Insect Cells Infected with a Baculovirus Expression Vector", Molecular and Cellular Biology, December 1983, Vol. 3, No. 12, p. 2156-2165; Pennock et al., "Strong and Regulated Expression of *Escherichia coli* B-Galactosidase in Infect Cells with a Baculovirus vector, "Molecular and Cellular Biology March 1984, Vol. 4, No. 3, p. 406; EPA0 370 573; U.S. Pat. No. 920,197, filed Oct. 16, 1986; EP Patent publication No. 265785; U.S. Pat. No. 4,769,331 (recombinant herpesvirus); Roizman, "The function of herpes simplex virus genes: A primer for genetic engineering of novel vectors," PNAS USA 93:11307-11312, October 1996; Andreansky et al., "The application of genetically engineered herpes simplex viruses to the treatment of experimental brain tumors," PNAS USA 93:11313-11318, October 1996; Robertson et al., "Epstein-Barr virus vectors for gene delivery to B lymphocytes", PNAS USA 93:11334-11340, October 1996; Frolov et al., "Alphavirus-based expression vectors: Strategies and applications," PNAS USA 93:11371-11377, October 1996; Kitson et al., J. Virol. 65, 3068-3075, 1991; U.S. Pat. Nos. 5,591,439, 5,552,143; WO 98/00166; allowed U.S. application Ser. Nos. 08/675,556, and 08/675,566 both filed Jul. 3, 1996 (recombinant adenovirus); Grunhaus et al., 1992, "Adenovirus as cloning vectors," Seminars in Virology (Vol. 3) p. 237-52, 1993; Ballay et al. EMBO Journal, vol. 4, p. 3861-65, Graham, Tibtech 8, 85-87, April 1990; Prevec et al., J. Gen Virol. 70, 42434; PCT WO 91/11525; Felgner et al. (1994), J. Biol. Chem. 269, 2550-2561, Science, 259:1745-49, 1993; and McClements et al., "Immunization with DNA vaccines encoding glycoprotein D or glycoprotein B, alone or in combination, induces protective immunity in animal models of herpes simplex virus-2 disease", PNAS USA 93:11414-11420, October 1996; and U.S. Pat. Nos. 5,591,639, 5,589,466, and 5,580, 859, as well as WO 90/11092, WO93/19183, WO94/21797, WO95/11307, WO95/20660; Tang et al., Nature, and Furth et al., Analytical Biochemistry, relating to DNA expression vectors, inter alia. See also WO 98/33510; Ju et al., Diabetologia, 41:736-739, 1998 (lentiviral expression system); Sanford et al., U.S. Pat. No. 4,945,050; Fischbach et al. (Intracel); WO 90/01543; Robinson et al., Seminars in Immunology vol. 9, pp. 271-283 (1997), (DNA vector systems); Szoka et al., U.S. Pat. No. 4,394,448 (method of inserting DNA into living cells); McCormick et al., U.S. Pat. No. 5,677,178 (use of cytopathic viruses); and U.S. Pat. No. 5,928,913 (vectors for gene delivery); as well as other documents cited herein.

Preferred viral vectors include baculovirus such as BaculoGold (BD Biosciences Pharmingen, San Diego, CA), in particular provided that the production cells are insect cells. Although the baculovirus expression system is preferred, it is understood by those of skill in the art that other expression systems, including those described above, will work for purposes of the present invention, namely the expression of recombinant protein.

Thus, in the context of the present invention, the "vector" is preferably a recombinant virus, preferably baculovirus, and/or the "nucleic acid sequence" is preferably a DNA sequence.

Preferably, in step (b) of the method as herein described and claimed the removing of a portion of the first liquid from said mixture consists of or comprises filtering said mixture with at least one filter, wherein said at least one filter preferably comprises a filter membrane.

According to another preferred aspect, in step (b) said concentrating comprises feeding the mixture into a filter system containing at least one filter, wherein the at least one filter comprises a filter membrane having a membrane pore size allowing the neutralized inactivating agent and/or the neutralizing agent to pass through while retaining the recombinant protein and/or said quaternary structures in the bulk flow, and discharging the permeate comprising the neutralized inactivating agent and/or the neutralizing agent.

According to a further preferred aspect, in step (c) said continuous diafiltration comprises feeding the solution into a filter system containing at least one filter, wherein the at least one filter comprises a filter membrane having a membrane pore size allowing the neutralized inactivating agent and/or the neutralizing agent to pass through while retaining the recombinant protein and/or said quaternary structures in the bulk flow, discharging the permeate comprising the neutralized inactivating agent and/or the neutralizing agent, and adding a second liquid to the bulk flow at a rate equal to the permeate flow, wherein the second liquid is different from the first liquid.

A "second liquid", for purposes of the present invention, refers to any liquid normally used in combination with cells, antigen, immunogenic compositions, vaccines, and the like, which is different from the first liquid. Preferably, the second liquid is an aqueous solution, even more preferably a pharmaceutically acceptable solution, and even more preferably a buffer, most preferably a physiologically acceptable buffer, such as a saline or phosphate buffer and the like, e.g. P-saline or PBS. Most preferably, the second liquid is characterized by not being virucidal to any live virus or live bacteria, when the live virus or live bacteria is cultivated in or stored in such a liquid.

Preferably, the at least one filter described herein is at least one flat sheet filter and/or at least one hollow fiber filter, wherein said at least one filter is most preferably at least one flat sheet filter. The at least one flat sheet filter is preferably at least one cassette filter.

In particular, the at least one filter are 2-8 filters, preferably 5-7 filters, and most preferably 6 filters and/or each of the at least one filter particularly has a total filter area of about 16-26 m², preferably of about 20-22 m², most preferably of about 21 m².

The filter membrane, as described herein, preferably has an average pore size that is smaller than the recombinant protein and/or smaller than said quaternary structures, and/or the filter membrane preferably has a molecular weight cut off of between about 200 kDa and about 500 kDa, in particular of about 300 kDa.

Preferably, the filter membrane consists of or comprises a material selected from the group consisting of polyethersulfone, cellulose hydrate, regenerated cellulose, stabilized cellulose, cross-linked cellulose, cross-linked cellulose hydrate, cellulose acetate, polyamide, polyurethane, polypropylene, polysulfone, polycarbonate, nylon, polyimide, and combinations thereof, and/or the filter membrane preferably consists of or comprises polyethersulfone, or the filter membrane is optionally a stabilized cellulose based membrane.

According to another preferred aspect of the present invention, in step (b) and in step (c) the same filter system is utilized. Thus, according to this preferred aspect, solely one filter system is used for both the concentrating of step (b) and the continuous diafiltration of step (c).

Preferably, the mixture remaining after step (c) comprises a concentration of the inactivating agent which is less than one thousands of the concentration of the neutralizing agent resulting from step (iii).

Furthermore, in the context of the present invention, it has been found that it is particularly preferred that step (iii) is carried out in a first container, and wherein the mixture resulting from neutralizing the inactivating agent is transferred from the first container to a second container connected with a filter system, and wherein after transferring the mixture from the first to the second container a valve between the first container and the second container is closed, and the empty first container is filled with the second liquid, in step (b) the mixture is circulated through the second container and the filter system until the concentrating is completed, and in step (c) the valve between the first and the second container is opened and the second liquid is continuously led from the first container to the second container while the mixture is circulated through the filter system and the second container.

In a further aspect, the present invention concerns a method as herein described and claimed, wherein the volume of the mixture resulting from step (a) is from 1000 L to 10000 L, preferably from 2000 L to 8000 L, and most preferably from 3000 L to 5000 L.

As mentioned herein, it is understood that "the volume of the mixture resulting from step (a)" is in particular equivalent to "the initial volume of the mixture in step (b) before said concentrating". In another aspect, the present invention concerns a method as herein described and claimed, wherein in step (b) said recombinant protein and/or said quaternary structures is finally concentrated at least 5×, preferably at least 8×, more preferably 9× to 11×, and most preferably about 10×, in comparison to the volume of the mixture resulting from step (a).

The concentrating step (b) of the methods provided herein can be performed such that the recombinant protein is, or said quaternary structures are, concentrated from 3× to 50× in comparison to the volume of the mixture resulting from step (a) or to the volume of the mixture resulting from step (iii), respectively. More preferably, said concentrating step can be done such that the recombinant protein is, or said quaternary structures are, concentrated at least 5×, such as from 5× to 20× in comparison to volume of the mixture resulting from step (a) or to the volume of the mixture resulting from step (iii), respectively. Still more preferably, said concentrating step can be done such that the recombinant protein is, or said quaternary structures are, concentrated at least 8×, such as from 8× to 14× in comparison to the volume of the mixture resulting from step (a) or to the volume of the mixture resulting from step (iii), respectively. Most preferably, said concentrating step is done such that the recombinant protein is, or said quarternary structures are, concentrated at least 10×, such as from 10× to 12× in comparison to the volume of the mixture resulting from step (a) or to the volume of the mixture resulting from step (iii), respectively.

Preferably, in step (c) the total volume of the second liquid added to the bulk flow is at least 5×, preferably at least 7×, more preferably at least 9×, and most preferably at least 10×, the volume of the solution resulting from step (b), and/or the total volume of the second liquid added to the bulk flow is most preferably about the volume of the mixture resulting from step (a).

In a further aspect, the present invention concerns a method as herein described and claimed, wherein said method further comprises the step of (d) admixing the mixture remaining after step (c) with a further component selected from the group consisting of pharmaceutically acceptable carriers, adjuvants, diluents, excipients, and combinations thereof, and wherein the concentration of the recombinant protein and/or the concentration of said quarternary structures in the solution resulting from said admixing is preferably about or below (e.g., 0.2×-0.5×) the concentration of the recombinant protein and/or said quarternary structures in the mixture resulting from step (a).

As mentioned herein, it is understood that "the concentration of the recombinant protein and/or said quarternary structures in the mixture resulting from step (a)" is in particular equivalent to "the initial concentration of the recombinant protein and/or said quarternary structures in the mixture in step (b) before said concentrating".

As used herein, "a pharmaceutical-acceptable carrier" includes any and all solvents, dispersion media, coatings, stabilizing agents, diluents, preservatives, antibacterial and antifungal agents, isotonic agents, adsorption delaying agents, and the like.

"Adjuvants" as used herein, can include aluminum hydroxide and aluminum phosphate, saponins e.g., Quil A, QS-21 (Cambridge Biotech Inc., Cambridge MA), GPI-0100 (Galenica Pharmaceuticals, Inc., Birmingham, AL), water-in-oil emulsion, oil-in-water emulsion, water-in-oil-in-water emulsion. The emulsion can be based in particular on light liquid paraffin oil (European Pharmacopea type); isoprenoid oil such as squalane or squalene; oil resulting from theoligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed. Stewart-Tull, D. E. S.). JohnWiley and Sons, NY, pp 51-94 (1995) and Todd et al., Vaccine 15:564-570 (1997). For example, it is possible to use the SPT emulsion described on page 147 of "Vaccine Design, The Subunit and Adjuvant Approach" edited by M. Powell and M. Newman, Plenum Press, 1995, and the emulsion MF59 described on page 183 of this same book. Further suitable adjuvants include, but are not limited to, the RIBI adjuvant system (Ribi Inc.), Block co-polymer (CytRx, Atlanta GA), SAF-M (Chiron, Emeryville CA), monophosphoryl lipid A, Avridine lipid-amine adjuvant, heat-labile enterotoxin from *E. coli* (recombinant or otherwise), cholera toxin, IMS 1314 or muramyl dipeptide among many others. Among the copolymers of maleic anhydride and alkenyl derivative, the copolymers EMA (Monsanto), which are copolymers of maleic anhydride and ethylene, are included. The dissolution of these polymers in water leads to an acid solution that will be neutralized, preferably to physiological pH, in order to give the adjuvant solution into which the immunogenic, immunological or vaccine composition itself will be incorporated.

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Phameuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name Carbopol; (BF Goodrich, Ohio, USA) are particularly appropriate. They are cross-linked with an allyl sucrose or with allyl pentaerythritol. Among then, there may be mentioned Carbopol 974P, 934P and 971P. Most preferred is the use of Carbopol 971P.

"Diluents" can include water, saline, dextrose, ethanol, glycerol, and the like.

"Isotonic agents" can include sodium chloride, dextrose, mannitol, sorbitol, and lactose, among others.

"Stabilizers" include albumin and alkali salts of ethylendiamintetracetic acid, among others.

A "preservative" as used herein refers to an anti-microbiological active agent, such as for example Gentamycin, Merthiolate, and the like. In particular adding of a preservative is most preferred for the preparation of a multi-dose composition. Those anti-microbiological active agents are added in concentrations effective to prevent the composition of interest for any microbiological contamination or for inhibition of any microbiological growth within the composition of interest.

Preferably, in step (d) said further component is a combination of an adjuvant, water and sodium chloride, in particular a combination of an adjuvant solution and P-saline, wherein said adjuvant is preferably a polymer of acrylic or methacrylic acid, and still more preferably a carbomer.

The term "P-saline", as mentioned herein, in particular relates to a buffer solution composed of 0.8-0.9% (w/v) NaCl, e.g. 0.85% (w/v) NaCl, dissolved in water and pH adjusted to 6.8-7.0.

In another aspect, the present invention concerns a method as herein described and claimed, wherein the mixture used for step (a) is obtainable by a procedure comprising the steps of (1) permitting infection of susceptible cells in culture with a vector comprising a nucleic acid sequence encoding said recombinant protein, wherein said recombinant protein is expressed by said vector, (2) thereafter recovering the recombinant protein and/or quaternary structures comprising a plurality of said recombinant protein from the cell culture, wherein preferably cell debris is separated from the recombinant protein and/or said quaternary structures via a separation step, preferably including a micro filtration through at least one filter, preferably two filters, wherein the at least one filter preferably has a pore size larger than the recombinant protein and/or quaternary structures containing a plurality of said recombinant protein, in particular has a pore size of about 1 to about 20 μm and/or about 0.1 μm to about 4 μm.

Preferably, in said method the separation step includes or consists of:

a micro filtration through one or more filters having a pore size of about 2 μm to about 15 μm, and/or a micro filtration through one or more filters having a pore size of about 0.8 μm to about 1.0 μm.

Preferred cells are those susceptible for infection with an appropriate recombinant viral vector, containing a recombinant protein DNA and expressing the recombinant protein. Preferably the cells are insect cells, and more preferably, they include the insect cells sold under the trademark SF+ insect cells (Protein Sciences Corporation, Meriden, CT). Preferred cell cultures have a cell count between about $0.3\text{-}2.0\times10^6$ cells/mL, more preferably from about $0.35\text{-}1.9\times10^6$ cells/mL, still more preferably from about $0.4\text{-}1.8\times10^6$ cells/mL, even more preferably from about $0.45\text{-}1.7\times10^6$ cells/mL, and most preferably from about $0.5\text{-}1.5\times10^6$ cells/mL.

The vector comprising a nucleic acid sequence encoding said recombinant protein has a preferred multiplicity of infection (MOI) of between about 0.03-1.5, more preferably from about 0.05-1.3, still more preferably from about 0.09-1.1, and most preferably from about 0.1-1.0, when used for the infection of the susceptible cells. Preferably the MOIs mentioned above relates to one mL of cell culture fluid. Preferably, the method described herein comprises the infection of $0.35\text{-}1.9\times10^6$ cells/mL, still more preferably of about $0.4\text{-}1.8\times10^6$ cells/mL, even more preferably of about $0.45\text{-}1.7\times10^6$ cells/mL, and most preferably of about $0.5\text{-}1.5\times10^6$ cells/mL with a recombinant viral vector containing a recombinant protein DNA and expressing the recombinant protein having a MOI (multiplicity of infection) of between about 0.03-1.5, more preferably from about 0.05-1.3, still more preferably from about 0.09-1.1, and most preferably from about 0.1-1.0.

Appropriate growth media will also be determinable by those of skill in the art with a preferred growth media being serum-free insect cell media such as Excell 420 (JRH Biosciences, Inc., Lenexa, KS) and the like.

In said method it is preferred that the cell culture in step (1) is maintained at 22-32° C., more preferably at about 24-30° C., still more preferably at about 25-29° C., even more preferably from about 26-28° C., and most preferably at 27° C., preferably while the recombinant protein is expressed by said vector, and/or that the recovering in step (2) occurs 5 to 8 days, most preferably 8 days, after inoculation of the cells with the vector and/or when cell viability decreases to less than 10%.

In another aspect, the present invention concerns a method as herein described and claimed, wherein said recombinant protein is selected from the group consisting of:

a recombinant PCV2 ORF2 protein preferably comprising or consisting of a sequence having at least 70%, at least 75%, at least 80%, at least 85%, at least 90%, at least 91%, at least 92%, at least 93%, at least 94%, at least 95%, at least 96%, at least 97%, at least 98%, at least 99%, at least 99.1%, at least 99.5%, or 100% sequence identity with the sequence of SEQ ID NO:1 or SEQ ID NO:2.

The term "having 100% sequence identity", as used herein, is understood to be equivalent to the term "being identical".

Percent sequence identity has an art recognized meaning and there are a number of methods to measure identity between two polypeptide or polynucleotide sequences. See, e.g., Lesk, Ed., *Computational Molecular Biology*, Oxford University Press, New York, (1988); Smith, Ed., *Biocomputing: Informatics And Genome Projects*, Academic Press, New York, (1993); Griffin & Griffin, Eds., *Computer Analysis Of Sequence Data, Part I*, Humana Press, New Jersey, (1994); von Heinje, *Sequence Analysis In Molecular Biology*, Academic Press, (1987); and Gribskov & Devereux, Eds., *Sequence Analysis Primer*, M Stockton Press, New York, (1991). Methods for aligning polynucleotides or polypeptides are codified in computer programs, including the GCG program package (Devereux et al., *Nuc. Acids Res.* 12:387 (1984)), BLASTP, BLASTN, FASTA (Atschul et al., *J. Molec. Biol.* 215:403 (1990)), and Bestfit program (Wisconsin Sequence Analysis Package, Version 8 for Unix, Genetics Computer Group, University Research Park, 575 Science Drive, Madison, Wis. 53711) which uses the local homology algorithm of Smith and Waterman (*Adv. App. Math.*, 2:482-489 (1981)). For example, the computer program ALIGN which employs the FASTA algorithm can be used, with an affine gap search with a gap open penalty of −12 and a gap extension penalty of −2. For purposes of the present invention, protein/amino acid sequences are aligned using Clustal W method in MegAlign software software version 11.1.0 (59), 419 by DNASTAR Inc. using the default multiple alignment parameters set in the program (Gonnet series protein weight matrix with Gap penalty=10.0, gap length penalty=0.2, and delay divergent sequence (%)=30%).

As used herein, it is in particular understood that the term "sequence identity with the sequence of SEQ ID NO:X" is equivalent to the term "sequence identity with the sequence of SEQ ID NO: X over the length of SEQ ID NO: X" or to the term "sequence identity with the sequence of SEQ ID NO:X over the whole length of SEQ ID NO: X", respectively. In this context, "X" is any integer selected from 1 to 2 so that "SEQ ID NO: X" represents any of the SEQ ID NOS mentioned herein.

It is further understood that the term "recombinant protein consisting of a sequence" in particular also concerns any cotranslational and/or posttranslational modification or modifications of the sequence affected by the cell in which the polypeptide is expressed. Thus, the term "recombinant protein consisting of a sequence", as described herein, is also directed to the sequence having one or more modifications effected by the cell in which the polypeptide is expressed, in particular modifications of amino acid residues effected in the protein biosynthesis and/or protein processing, preferably selected from the group consisting of glycosylations, phosphorylations, and acetylations.

In another aspect, the present invention concerns a method as herein described and claimed, wherein said quaternary structures comprising a plurality of said recombinant protein are virus-like particles comprising a plurality of a recombinant PCV2 ORF2 protein.

In another aspect, the present invention concerns a method as herein described and claimed, wherein the virucidal activity of the mixture resulting from said method is reduced by at least 20% as compared to the mixture that has not undergone the concentrating of step (b) and the continuous diafiltration of step (c) of said method, and/or wherein the immunogenic composition produced by said method causes a loss of less than 1 log $TCID_{50}$ per mL of a live virus, when the live virus is mixed with the immunogenic composition for four or more hours, in particular at room temperature. "Room temperature", as mentioned herein, in particular relates to 20 to 25 degrees Celsius, and more particular to (an average of) 23° C.

In another aspect, the present invention concerns a method as herein described and claimed, wherein the live virus is Porcine Reproductive and Respiratory Syndrome (PRRS) virus.

In another aspect, the present invention concerns a method as herein described and claimed, wherein the method further comprises the step of combining the mixture remaining after step (c) and/or step (d) with at least one additional antigen, wherein the at least one additional antigen is preferably a Porcine Reproductive and Respiratory Syndrome (PRRS) virus. In the context of the present invention it is in particular understood that the term "remaining after step" is equivalent to "resulting from step".

The present application does not only provide a method of producing an immunogenic composition, it also relates to the immunogenic composition produced by the method as herein described and claimed.

In another aspect, the present invention thus concerns an immunogenic composition obtainable by a method as herein described and claimed.

According to a particular preferred aspect, said immunogenic composition is a solution comprising 1-10 μM L-arginine and/or 1-10 μM L-lysine, and most preferably said immunogenic composition is a solution comprising 1-10 μM L-arginine and 1-10 μM L-lysine.

Thus, the present invention also provides an immunogenic composition comprising recombinant PCV2 ORF2 protein, preferably consisting of or comprising a sequence having at least 90%, at least 91%, at least 92%, at least 93%, at least 94%, at least 95%, at least 96%, at least 97%, at least 98%, at least 99%, at least 99.1%, at least 99.5%, or 100% sequence identity with the sequence of SEQ ID NO:1 and/or SEQ ID NO:2, and 1-10 μM L-arginine and/or 1-10 μM L-lysine, and wherein optionally the immunogenic composition is substantially free from a neutralized inactivating agent and/or substantially free from a neutralizing agent.

It is understood that "1-10 μM", as used herein, is in particular equivalent to "from 1 μM up to 10 μM".

In particular, the immunogenic composition or mixture resulting from step (d) comprises 4-400 μg recombinant PCV2 ORF2 per mL or preferably 8-200 μg recombinant PCV2 ORF2 protein per mL.

"Substantially free from a neutralizing agent" is in particular understood to mean that the immunogenic composition comprises less than 150 nM of the neutralizing agent. Thus, for instance, the indication that "the immunogenic composition is substantially free from sodium thiosulfate" is in particular understood to be equivalent with the specification that "the immunogenic composition comprises less than 150 nM sodium thiosulfate".

According to a further aspect, the present invention thus concerns an immunogenic composition obtainable by a method as herein described and claimed, wherein the immunogenic composition or mixture resulting from step (d) is substantially free from sodium thiosulfate or comprises less than 150 nM sodium thiosulfate.

Further, an immunogenic composition is provided, in particular the immunogenic composition obtainable by a method as herein described and claimed, preferably obtainable by any such method comprising step (d), wherein the immunogenic composition comprises
a recombinant PCV2 ORF2 protein preferably comprising or consisting of a sequence having at least 90%, at least 91%, at least 92%, at least 93%, at least 94%, at least 95%, at least 96%, at least 97%, at least 98%, at least 99%, at least 99.1%, at least 99.5%, or 100% sequence identity with the sequence of SEQ ID NO:1 and/or SEQ ID NO:2, and 0.1-1 μM L-Tryptophane; and/or
    0.1-3 μM L-Glutamine; and/or
    0.2-4 μM L-Methionine; and/or
    1-10 μM L-Arginine; and/or
    1-10 μM L-Threonine; and/or
    1-15 μM L-Lysine.

Preferably, the immunogenic composition as herein described and claimed comprises 0.1-0.7 μM L-Tryptophane; and/or
    0.7-2.4 μM L-Glutamine; and/or
    0.5-3.2 μM L-Methionine; and/or
    1.4-4.7 μM L-Arginine; and/or
    1.6-8.0 μM L-Threonine; and/or
    4.0-12.2 μM L-Lysine.

More preferably, the immunogenic composition as herein described and claimed comprises 0.2-0.6 μM L-Tryptophane; and/or
    0.8-2.2 μM L-Glutamine; and/or
    0.8-2.2 μM L-Methionine; and/or
    1.6-4.3 μM L-Arginine; and/or
    2.4-6.3 μM L-Threonine; and/or
    4.4-11.2 μM L-Lysine.

According to a particularly preferred aspect, the immunogenic composition as herein described and claimed comprises 0.7-2.4 μM L-Glutamine and 4.0-12.2 μM L-Lysine, or preferably comprises 0.8-2.2 μM L-Glutamine and 4.4-11.2 μM L-Lysine.

Preferably, the immunogenic composition as herein described and claimed is substantially free from sodium thiosulfate.

According to a further preferred aspect, an immunogenic composition is provided, in particular the immunogenic composition obtainable by a method as herein described and claimed, preferably obtainable by any such method comprising step (d), wherein the immunogenic composition when subjected to a 2 dimensional (2 D) Ultra Performance Liquid Chromatography (UPLC) at room temperature exhibits a ratio of the peak A area to the peak B area of 0.2-0.4 and/or a ratio of the peak C area to the peak B area of 0.5-0.9, wherein the 2 D UPLC comprises a first dimension of chromatography with a system volume of 400 μL, wherein
        a sample comprising the immunogenic composition is injected into an anion exchange column with 0.1 mL column volume packed with quarternary amine-functionalized material suitable for binding virus like-particles, and
        a multi step gradient method of initial 100% 50 mM Tris, pH 8 at 0 minutes to 97.5% 50 mM Tris, pH 8 and 2.5% 50 mM Tris, 2 M NaCl, pH 8 at 1 minute and finally to 10% 50 mM Tris, pH 8 and 90% 50 mM Tris, 2M NaCl, pH 8 at 2 minutes is driven with a flow rate of 0.6 mL/min through the anion exchange column,
and wherein at the retention time of 2.67 min it is switched from the first dimension of chromatography to
    a second dimension of chromatography, wherein 50 μL eluate of the first dimension of chromatography are driven with a flow rate of 0.3 mL/min through a size exclusion column with a 1.75 mL column volume with a pore size of 450 Å,
    and wherein a chromatogram is recorded by monitoring the fluorescence emission at the wavelength of 330 nm and an excitation wavelength of 280 nm, and wherein
        the peak A area is the peak area of the highest peak at the retention time of 0-1 minutes in the chromatogram;
        the peak B area is the peak area of the highest peak at the retention time of 7-8 minutes in the chromatogram;
        the peak C area is the peak area of the highest peak at the retention time of 8.5-9.5 minutes in the chromatogram.

According to one preferred aspect, said sample comprises the immunogenic composition diluted in 50 mM Tris, pH 8. For instance, in case said sample comprises the immunogenic composition remaining after step (c), then the sample preferably comprises or consists of the immunogenic composition diluted 1:10 in 50 mM Tris, pH 8.

The quarternary amine-functionalized material suitable for binding virus like-particles is preferably a large pore and/or a non porous material.

Example 5 describes such a 2 D UPLC method that can be used by a person skilled in the art. In cases of controversial results and in any question of doubt, ratios of peak areas as mentioned herein, refer to those which are/can be estimated by the method as described in Example 5.

The term "immunogenic composition" means, but is not limited to, a composition of matter that comprises at least one antigen which elicits a cellular and/or antibody-mediated immune response in a host against the antigen of interest. Usually, an "immune response" includes but is not limited to one or more of the following effects: the production or activation of antibodies, B cells, helper T cells, suppressor T cells, and/or cytotoxic T cells and/or gamma-delta T cells, directed specifically to an antigen or antigens included in the composition or vaccine of interest. Preferably, the host will display either a therapeutic or protective immune response such that resistance to new infection will be enhanced and/or the clinical severity of the disease reduced. In such a case the immunogenic composition is a "vaccine". Such protection will be demonstrated by either a reduction or lack of symptoms normally displayed by an infected host, a quicker recovery time and/or a lowered viral titer in the infected host. The host, as described herein, is in particular a mammal, preferably a pig.

In a further aspect, the virucidal activity of the immunogenic composition produced by the method as herein described and claimed is reduced by at least 10%, preferably by at least 20%, as compared to a corresponding immunogenic composition that has not undergone the concentrating of step (b) and the continuous diafiltration of step (c) of said method. More preferably, the virucidal activity of the immunogenic composition is reduced by at least 50% as compared to a corresponding immunogenic composition that has not undergone the concentrating of step (b) and the continuous diafiltration of step (c). Still more preferably, the virucidal activity of the immunogenic composition is reduced by at least 70% as compared to a corresponding immunogenic composition that has not undergone the concentrating of step (b) and the continuous diafiltration of step (c). Even still more preferably, the virucidal activity of the immunogenic composition is reduced by at least 90% as compared to a corresponding immunogenic composition that has not undergone the concentrating of step (b) and the continuous diafiltration of step (c).

For the purpose of the current invention the term "virucidal activity" means, that a liquid, fluid, solution, composition or the like inactivates or kills live viruses or live bacteria to a certain extent, when said liquid, fluid, solution, composition or the like is mixed with such live viruses or live bacteria. Thus, a reduction of the virucidal activity of a liquid, fluid, solution, composition or the like by at least 10% means, that the survival rate of live viruses or live bacteria is 90% higher in a liquid, fluid, solution, composition or the like that has undergone any of the production methods described herein, as compared to a liquid, fluid, solution, composition or the like, that has not undergone any of such production methods. In the present context "survival rate" in particular relates to the percentage of viruses or bacteria maintaining the capability to replicate in a host.

According to a particular preferred aspect, the immunogenic composition produced by the method as herein described and claimed causes a loss of less than 1 log $TCID_{50}$ of a live virus or less than 1 log CFU per mL of a live bacterium, when the live virus or live bacterium is mixed with said immunogenic composition and incubated for at least 4 hours. More preferably, the immunogenic composition produced by the method as herein described and claimed causes a loss of less than 0.9 log $TCID_{50}$ per mL of a live virus or less than 0.9 log CFU per mL of a live bacterium, when the live virus or live bacterium is mixed and incubated with said immunogenic composition for at least 4 hours. Even more preferably, the immunogenic composition produced by the method as herein described and claimed causes a loss of less than 0.7 log $TCID_{50}$ per mL of a live virus or less than 0.7 log CFU per mL of a live bacterium, when the live virus or live bacterium is mixed and incubated with said immunogenic composition for at least 4 hours. Still more preferably, the immunogenic composition produced by the method as herein described and claimed causes a loss of less than 0.5 log $TCID_{50}$ per mL of a live virus or less than 0.5 log CFU per mL of a live bacterium, when the live virus or live bacterium is mixed and incubated with said immunogenic composition for at least 4 hours. Even more preferably, the immunogenic composition produced by the method as herein described and claimed causes a loss of less than 0.3 log $TCID_{50}$ per mL of a live virus or less than 0.3 log CFU per mL of a live bacterium, when the live virus or live bacterium is mixed and incubated with said immunogenic composition for at least 4 hours.

The $TCID_{50}$ per mL can be estimated by a standard in vitro titration assay which allows the estimation of the amount of a live virus. The CFU per mL can be determined also by a standard in vitro titration assay which allows the estimation of the amount of a live bacterium. The term "per mL" preferably refers to 1 mL of a fluid.

Furthermore, it has been found that the immunogenic composition obtainable by the method as herein described and claimed is particularly stable.

According to a particular preferred aspect, the shelf life of the immunogenic composition produced by the method as herein described and claimed is at least 2 years, preferably at least 3 years, wherein the term "shelf-life" as used herein means a period that a product can be stored without the quality falling below a certain minimum acceptable level.

In particular, the present invention concerns an immunogenic composition, wherein the immunogenic composition induces, preferably in a pig, a protective immune response against the pathogen from which the amino acid sequence of the recombinant protein is derived, wherein the pathogen is preferably PCV2, after the administration of one dose of the immunogenic composition, and wherein said administration is preferably an administration of one dose of the immunogenic composition to a pig.

In another aspect, the present invention concerns an immunogenic composition as herein described and claimed, wherein the immunogenic composition further comprises an attenuated live virus, preferably an attenuated Porcine Reproductive and Respiratory Syndrome (PRRS) virus, or an attenuated live bacterium.

"Live" virus or bacterium, for purposes of the present invention, refers to a virus or bacterium that is capable of replicating in a host. A preferred live virus and a preferred live bacterium of the present invention are the PRRS virus (PRRSV) and the *Mycoplasma hyopneumonia* bacterium, respectively. However, the term live virus or live bacterium is not limited to PRRSV and *Mycoplasma hyopneumoniae*, respectively.

In another aspect, the present invention concerns an immunogenic composition as herein described and claimed, wherein the immunogenic composition further comprises an attenuated Porcine Reproductive and Respiratory Syndrome (PRRS) virus.

The term "attenuated" in particular relates to viruses or bacteria that have been cultured in a way so as to reduce their virulence and make them suitable for use as vaccines. Thus, more particular "attenuated" relates to a virus or bacterium which is alive but, preferably due to reduction in virulence or toxicity by mean of such special cultivation, can no longer produce disease.

Preferably, said immunogenic composition induces, in particular in a pig, a protective immune response against PRRS virus after the administration of one dose of the immunogenic composition, and wherein said administration is preferably an administration of one dose of the immunogenic composition to a pig.

More preferably, said immunogenic composition induces, in particular in a pig, a protective immune response against PCV2 and PRRS virus after the administration of one dose of the immunogenic composition, and wherein said administration is preferably an administration of one dose of the immunogenic composition to a pig.

In another aspect, the present invention also provides a kit, wherein the kit comprises a container containing the immunogenic composition as herein described and claimed, and wherein the kit preferably further comprises at least one additional container containing at least one additional antigen selected from the group consisting of attenuated live virus, preferably attenuated PRRS virus, and attenuated live bacterium.

According to a further aspect, a kit comprising a container containing the immunogenic composition as herein described and claimed is provided.

The immunogenic composition as herein described and claimed and/or the kit as herein described and claimed may further comprise at least one additional antigen, preferably a viral or bacterial antigen, and even more preferably a viral or bacterial antigen from at least one other pathogen causing disease in swine. The additional antigen can be any one of those disclosed in the international patent application WO2007/094893 (the contents and teachings of which are hereby incorporated by reference). Briefly, the additional antigens can be antigens of any other pathogen causing disease in swine. Preferably, the "any other pathogen causing disease in swine" or the at least one other pathogen causing disease in swine is selected from the group consisting of: *Actinobacillus pleuropneumonia* (1); Adenovirus (2); Alphavirus such as Eastern equine encephalomyelitis viruses (3); *Bordetella bronchiseptica* (4); *Brachyspira* spp. (5), preferably *B. hyodysentheriae* (6); *B. piosicoli* (7), *Brucella suis*, preferably biovars 1, 2, and 3 (8); Classical swine fever virus (9); *Clostridium* spp. (10), preferably *Cl. difficile* (11), *Cl. perfringens* types A, B, and C (12), *Cl. novyi* (13), *Cl. septicum* (14), *Cl. tetani* (15); Coronavirus (16), preferably Porcine Respiratory Corona virus (17); *Eperythrozoonosis suis* (18); *Erysipelothrix rhusiopathiae* (19) *Escherichia coli* (20); *Haemophilus parasuis*, preferably subtypes 1, 7 and 14 (21) *Hemagglutinating encephalomyelitis* virus (22); Japanese Encephalitis Virus (23); *Lawsonia intracellularis* (24) *Leptospira* spp. (25), preferably *Leptospira australis* (26); *Leptospira canicola* (27); *Leptospira grippotyphosa* (28); *Leptospira icterohaemorrhagicae* (29); and *Leptospira interrogans* (30); *Leptospira pomona* (31); *Leptospira tarassovi* (32); *Mycobacterium* spp. (33) preferably *M. avium* (34), *M. intracellulare* (35) and *M. bovis* (36); *Mycoplasma hyopneumoniae* (37); *Pasteurella multocida* (38); Porcine cytomegalovirus (39); Porcine Parvovirus (40); Porcine Reproductive and Respiratory Syndrome Virus (41); Pseudorabies virus (42); Rotavirus (43); *Salmonella* spp. (44), preferably *S. thyhimurium* (45) and *S. choleraesuis* (46); *Staph. hyicus* (47); *Staphylococcus* spp. (48) preferably *Streptococcus* spp. (49), preferably *Strep. suis* (50); Swine herpes virus (51); Swine Influenza Virus (52); Swine pox virus (53); Swine pox virus (54); Vesicular stomatitis virus (55); Virus of vesicular exanthema of swine (56); *Leptospira hardjo* (57); *Mycoplasma hyosynoviae* (58); and/or combinations thereof.

Most preferably, the immunogenic composition as herein described and claimed and/or the kit as herein described and claimed further comprises one or more attenuated or inactivated non-PRRSV pathogens or antigenic material thereof.

In another aspect, the present invention concerns the immunogenic composition as herein described and claimed and/or the kit as herein described and claimed for use as a medicament, preferably as a vaccine.

In a further aspect, the present invention concerns the immunogenic composition as herein described and claimed and/or the kit as herein described and claimed, for use in a method of inducing a protective immune response against at least one pathogen and/or reducing one or more clinical signs of at least one pathogen infection in an animal, preferably in a pig.

The present invention further provides a method of inducing a protective immune response against at least one pathogen and/or reducing one or more clinical signs of at least one pathogen infection in an animal, wherein the immunogenic composition as herein described and claimed is administered to an animal, in particular to a pig.

According to yet a further aspect, the present invention relates to the use of the immunogenic composition as herein described and claimed for the preparation of a medicament for inducing a protective immune response against at least one pathogen and/or reducing one or more clinical signs of at least one pathogen infection in an animal, preferably in a pig.

Preferably, the at least one pathogen is selected from the group consisting of PCV2, PRRSV, non-PRRSV pathogens, and combinations thereof.

The term "non-PRRSV pathogens", as used herein, in particular relates to pathogens selected from *Mycoplasma hyopneumoniae*, Pseudorabies virus, Porcine influenza virus, Porcine parvovirus, Transmissible gastroenteritis virus, *Escherichia coli, Erysipelothrix rhusiopathiae, Bordetella bronchiseptica, Salmonella cholerasuis, Haemophilus parasuis, Pasteurella multocida, Streptococcus suis* and *Actinobacillus pleuropneumoniae.*

The term "reducing one or more clinical signs", as used herein, shall in particular mean that any of such signs are reduced in incidence or severity in animals receiving an administration of the immunogenic composition in comparison with a "control group" of animals when both have been infected with or challenged by the pathogen from which the immunological active component(s) in the immunogenic composition is/are derived and wherein the control group has not received an administration of the immunogenic composition. In this context, the term "reduced" means a reduction of at least 10%, preferably 25%, even more preferably 50%, most preferably of 100% in the group having received the immunogenic composition as compared to the control group.

As used herein, "clinical signs" shall refer to signs of infection from pathogens that are directly observable from a live animal such as symptoms. Representative examples will depend on the pathogen selected but can include things such as nasal discharge, lethargy, coughing, elevated fever, reduced weight gain or weight loss, dehydration, diarrhea, swelling, lameness, and the like.

As used herein, a "protective immune response" refers to a reduced incidence of or reduced severity of clinical, pathological, or histopathological signs or symptoms of infection from a pathogen of interest up to and including the complete prevention of such signs or symptoms.

EXAMPLES

Example 1

Production of PCV2 ORF2 Protein—Upstream Processing

The PCV2 ORF2 protein is produced in baculovirus-infected SF+ cells in a process corresponding to the process described in WO 2006/072065 A2, Examples 1 to 3. In the following, this process is summarized:

PCV2 ORF2 baculovirus-vector is produced in bioreactors. The medium is added pre sterilized or sterile-filtered into the bioreactor. The medium is added with SF+ cells originating from expansion cultures. The cells are simultaneously inoculated (concurrent infection) upon planting with PCV2 ORF2 seed. Throughout the virus propagation temperature is maintained at 27±2° C. and pH is monitored. Dissolved Oxygen (DO) is controlled by sparging cleaned-compressed air, and oxygen ($O_2$). The harvest window occurs between 6 to 8 days after virus infection and the harvest criterion of ≤20% Cell Viability is achieved. At harvest, PCV2 ORF2 antigen fluids are clarified using two sets of filters, a pre-filter of 2.0-15.0 μm pore size and a final filter of 0.8-1.0 μm pore size. The filtered harvest fluids are collected in a tank. For the inactivation of the baculovirus, 5 mM BEI is added for up to 96 hours prior to neutralization. For the neutralization of the remaining BEI, 5 mM sodium thiosulfate is added to neutralize the BEI. Addition of sodium thiosulfate occurs 72-96 hours post inactivation.

Production of PCV2 ORF2 Protein—Downstream Processing

Laboratory Scale

A 3 L sample resulting from the above-described upstream process was taken to the laboratory and concentrated to 300 mL based on volume to achieve a 10 fold concentration. After concentration, the antigen was then diafiltered using 3 L of P-saline, which is a buffer solution composed of 0.85% NaCl dissolved in water and pH adjusted to 6.8-7.0.

Laboratory scale of the concentration and continuous diafiltration was performed under a Biosafety Cabinet, or BSC, at room temperature (27±2° C.) using a tangential flow filter (TFF) system composed of the following: TFF System Sartoflow Slice 200 Benchtop system, assembled with 1 Sartoslice Ultrafilter (UF) Cassette filter (PES, 200 cm$^2$ filtration area, 300 kD cut-off).

Before the ultrafiltration/diafiltration the TFF system was rinsed with 1 M NaOH (for at least 1 h), and the cassettes were chemically sterilized overnight with 0.1 NaOH. Then, the sterilized system and filters were placed in the BSC in order to assemble aseptically, and the inlet, outlet and permeate lines were connected. Permeate lines were connected to a waste bottle, while inlet lines were connected to the inactivated antigen to be concentrated. The outlet line stemmed from the filtration unit back into a retention bottle. The filter was equilibrated using sterile PBS (10 L per filter).

The product was concentrated by ultrafiltration to 10 times the original antigen volume based on volume. Flow rate through the filter varied as the antigen processed through concentration. At a small scale level, flow rate is a range and held by placing backpressure onto the system. The diafiltration was done with a 10-fold volume of the ultrafiltration volume against P-saline, wherein the P-saline was added at a rate equal to the permeate flow. The final concentrated and diafiltered antigen was stored at 2-8° C.

Utilizing a HPLC quantification method it was seen that this process had eliminated ≥99% of any residual insect cell media (ExCell 420 media), and had reduced neutralized BEI and the residual sodium thiosulfate to non-detectable levels.

Also, initial experiments had shown that in the context of the production of an immunogenic composition, as described herein, the use of flat sheet filters, as compared to hollow fiber filters, for the TFF system have the advantageous effect that storage costs will be significantly reduced since less storage bags/barrels (200 L) are needed to be utilized. In addition, it was seen that by using flat sheet filters manpower for harvest is significantly decreased as well as production time.

Operations Scale

In an operational or large scale processing (c.f. FIG. 1), approximately 4000 L resulting from the above-described upstream process are used. The system is designed so that the antigen containing solution in the inactivation tank can directly be sent to a downstream processing (DSP) tank at a continuous feed rate until the inactivation tank is empty.

The DSP tank is a repository for the antigen in process and for the final antigen presentation. The programmed weight of this tank controls the entire system in that when certain programmed weights are reached, the process will progress forward. In addition, this tank is where the final antigen product is collected and harvested into 200 L barrels for storage.

The DSP tank is connected to the microfiltration (MF) unit. After sending the antigen containing solution from the DSP tank to the MF unit, the antigen is concentrated and the retentate is sent back to the DSP tank while the permeate is transferred to waste.

The process starts by taking the weight of the inactivation tank containing the (intermediate) product resulting from the upstream processing. The 10 fold concentration is calculated based on the initial weight of the tank and programmed into the system operational unit for the MF unit. Once the concentration has started, the system triggers the transfer lines between the inactivation tank and the DSP tank to open or close based on tank weight. Upon the inactivation tank becoming empty, the system triggers the tank to close the transfer line to the DSP tank. After the inactivation tank is empty, a separate transfer line is activated in order for saline to be added into the recently evacuated inactivation tank. The saline is also monitored by weight, as the desired amount of saline to transfer to the DSP tank is the original weight taken and used for the concentration calculation. The retentate is fed back to the DSP tank and further passed over the MF unit again so as to further concentrate the retentate, until the weight of the retentate has decreased to the programmed value indicating the desired concentration.

The MF unit is unique in that it can support both microfilter cassettes as well as ultrafilter cassettes. For this procedure, a total of 6 ultrafilter sartocubes (at 21 m$^2$ per cube) are seated into the MF unit. This surface area was chosen after extensive evaluations of the system. There is a feed line into the MF unit from the DSP tank, a retentate line feeding back into the DSP tank and permeate-to-waste transfer line. This unit is programmed to run with a permeate pressure of 0 psi, while maintaining a recirculation of 20-35 psi with a target of 29 psi transmembrane pressure (TMP). The recirculation pump is run at 100% capacity until the hold mode is activated. These parameters are targeted during the concentration and diafiltration processes. The MF unit is activated to start the concentration step once the DSP tank is at a set weight and will keep the antigen in circulation until the set 10 fold concentration is achieved. Once the 10 fold concentration is complete, the MF unit is switched to the hold mode in order to circulate antigen at a reduced pressure and speed while the inactivation tank is being filled with the P-saline. After the P-saline has reached the desired volume in the inactivation tank which was the original weight at start, the system will initiate the diafiltration process by starting the influx of the P-saline into the DSP tank and the MF unit will ramp back up to the target ranges.

Once the inactivation tank is empty, the valve between the inactivation tank and DSP tank closes and the antigen is further processed through the MF unit until a 10 fold diafiltration is achieved. The concentrated and diafiltered antigen are in the DSP tank and pumped into antigen harvest barrels for the final repository. These barrels are stored at 4±2° C. until vaccine blending.

The product resulting from the above upstream and downstream processing was then finally mixed with a carbomer solution (adjuvant) and physiological saline (P-saline). This investigational veterinary product is hereinafter also termed investigational veterinary product (IVP) No. 1 or "IVP1", respectively.

In conclusion, regarding the new process described herein particular advantages seen were time savings, reduction in handling, and storage/space savings in the cooler.

Example 2

In Use Stability Studies

SUMMARY

Utilizing an optimized protocol a study was designed to investigate the in-use stability of an investigational veterinary product (lyophilisate) including a modified-live PRRS virus (said investigational vaccine product being also termed "IVP2" hereinafter) after reconstitution with the investigational veterinary product (IVP) No. 1 (IVP1) of Example 1.

An overview on the investigational veterinary products (IVPs) used is provided in Table 1.

The evaluation included two batches of IVP1 (one manufactured with a high potency and one at usual/standard release potency) and two batches of IVP2.

All investigational veterinary products (IVPs) tested (c.f. Table 1) were stored at 5° C.±3° C. until being used for the study.

In the study, each batch of IVP2 vaccine was reconstituted with IVP1, and the PRRS virus titer was tested at 0, 2 and 4 hours after reconstitution.

For each IVP2 batch, PRRS virus titers after reconstitution at time 0 were similar irrespective of the lyophilisate being reconstituted with WPBS (wash phosphate buffered saline (=phosphate bufferend saline wash solution)) or with IVP1 and irrespective of the scientists. In addition, testing results, after 2 and 4 hours post incubation at room temperature, did show no to negligible change in virus titers.

The results of the study support the associated use of IVP1 with IVP2.

1. Introduction

The study was designed to demonstrate the in-use stability of IVP2 after reconstitution with IVP1. IVP2 is a freeze-dried modified-live vaccine (MLV) and IVP1 was produced as described above.

In the following, the results of the in-use stability evaluation of IVP2 after reconstitution with IVP1 are shown.

2. Objective(S)/Purpose of the Studies

The objective of this in-use stability study was to investigate the stability of IVP2 vaccine after reconstitution with IVP1.

3. Materials

Two batches of each of the two vaccines evaluated and one batch of diluent control used in the study were used, wherein the compositions of the test materials are listed in Table 1.

| Material | Ingredient | Quantity Test Batch #1 | Test Batch #2 |
|---|---|---|---|
| IVP1 | PCV2 antigen | 7% | 3.2% |
| | Carbomer solution (Adjuvant) | 20% | 20% |
| | Physiological Saline | 73% | 76.8% |

-continued

| Material | Ingredient | Quantity Test Batch #1 | Test Batch #2 |
|---|---|---|---|
| IVP2 | PRRS virus | 75% | 75% |
| | Sucrose/Gelatin (Stabilizer) | 25% | 25% |
| | Physiological Saline | 0% | 0% |
| WPBS | Sodium Chloride | 8.00 mg/mL | |
| | Potassium Chloride | 0.20 mg/mL | |
| | Potassium Phosphate Monobasic, EP | 0.2 mg/mL | |
| | Sodium Phosphate Dibasic, Anhydrous | 1.15 mg/mL | |
| | Water for Injection | Q.S. to 1 mL | |

4. Design of the Study

Each batch of IVP2 vaccine was tested with each batch of the subunit vaccine (IVP1), in all possible combinations. Table 2.1 lists all eight vaccine combinations evaluated in this study.

TABLE 2.1

| | | List of the combinations of IVPs evaluated | |
|---|---|---|---|
| | | IVP combinations | |
| Sample No. | Sample ID* | IVP1 (batch #1 or #2) | IVP2 (batch #1 or #2) |
| 1 | IVP1#1__IVP2#1 | #1 | #1 |
| 2 | IVP1#2__IVP2#1 | #2 | #1 |
| 3 | IVP1#1__IVP2#2 | #1 | #2 |
| 4 | IVP1#2__IVP2#2 | #2 | #2 |

The samples were tested for PRRS virus titers immediately after complete reconstitution and pooling at time zero (T0). The pooled samples were stored at room temperature in the dark and tested again at 2 hours (T2) and at 4 hours (T4). Samples were prepared on the same day as testing. Each sample was tested in two different sessions and sessions were performed on different days.

Testing was performed by two scientists. Scientist 1 tested Samples No. 1 to 4 with IVP2 batch #1 and Scientist 2 tested Samples No. 5 to 8 with IVP2 batch #2. Each scientist tested two samples and an in-use stability control per session. The control consisted of IVP2 reconstituted with sterile wash phosphate buffered saline (WPBS) using the same volumes and time intervals as those indicated for the corresponding Test samples.

5. Methods 5.1 Reconstitution Method

For Each Sample (as Described in Table 2.1), Each of Three Vials of IVP2 was Reconstituted with 10 mL of IVP1. For each control, each of three vials of IVP2 was reconstituted with 10 ml of WPBS. After reconstitution was complete, the contents of each of the three vials, as described above, were pooled prior to initiating testing.

5.2 Testing Method

Day −3

A cell culture suspension of AK-MA104 cells was prepared in MEM supplemented with 10% FBS and gentamycin sulfate. 100 μL cell culture were seeded into each well of 96-well microtiter plates. The plates were closed with the lid and kept in the incubator for 3 days.

Day 0

Sample Preparation

The samples of IVP1 and of the positive control were used for resuspending the lyophilized samples of IVP2. The three vials were pooled and the pool titered in triplicate.

Titration

As dilution medium MEM supplemented with 2% FBS and gentamycin sulfate was used for diluting the samples.

Inoculation

The wells of the samples were inoculated with 100 µL of diluted sample and the wells of the negative control were inoculated with 100 µL media.

Incubation

It was incubated for 8 days in the incubator.

Day +8

Reading and Calculation

The final cytopathic effect (CPE) reading of the plates was made under inverse microscope, and the raw data was converted to the titer per 1 mL dose by addition of 1.0 log.

Titers were calculated according to the Reed and Muench method (Reed, L. J.; H. Muench, (1938). "A simple method of estimating fifty percent endpoints." Am. J. Hygiene, 27:493-497) and expressed as log 10 TCID50 per 1 mL dose. The titer of each sample at each testing interval was reported as the arithmetic mean titer per dose of the independent titrations of two consecutive valid test sessions with three independent titrations per session.

6. Acceptance Criteria

Virus titers of IVP2 obtained at 0 (T0), 2 (T2) and 4 (T4) hours after reconstitution with WPBS diluent control is greater than or equal to a predetermined/previously determined minimum immunizing dose (MID).

7. Results

Summary of mean titers obtained for the Test samples and respective controls at each incubation time (T0, T2 and T4) and corresponding titer differences relative to time 0 (T0-T0, T2-T0, and T4-T0) are shown in Table 3 and Table 4, respectively.

TABLE 3

| | Mean Virus Titers | | | |
|---|---|---|---|---|
| Sample Set | Sample Description | T0 | T2 | T4 |
| 1-1 | IVP2#1__WPBS control 1-1 | 6.10 | 5.97 | 6.06 |
| | IVP1#1__IVP2#1 | 6.13 | 6.01 | 6.10 |
| 1-2 | IVP2#1__WPBS control 1-2 | 6.12 | 6.21 | 6.11 |
| | IVP1#2__IVP2#1 | 6.06 | 6.09 | 6.07 |
| 2-1 | IVP2#2__WPBS control 2-1 | 6.01 | 6.01 | 6.04 |
| | IVP1#1__IVP2#2 | 5.93 | 6.02 | 6.04 |
| 2-2 | IVP2#2__WPBS control 2-2 | 5.94 | 5.98 | 5.86 |
| | IVP1#2__IVP2#2 | 5.94 | 5.87 | 5.85 |

TABLE 4

| | Mean Virus Titer Differences from T0 | | |
|---|---|---|---|
| Sample Set | Sample Description | T2 – T0 | T4 – T0 |
| 1-1 | IVP2#1__WPBS control 1-1 | −0.13 | −0.04 |
| | IVP1#1__IVP2#1 | −0.12 | −0.03 |
| 1-2 | IVP2#1__WPBS control 1-2 | 0.09 | −0.01 |
| | IVP1#2__IVP2#1 | 0.03 | 0.01 |

TABLE 4-continued

| | Mean Virus Titer Differences from T0 | | |
|---|---|---|---|
| Sample Set | Sample Description | T2 – T0 | T4 – T0 |
| 2-1 | IVP2#2__WPBS control 2-1 | 0.00 | 0.03 |
| | IVP1#1__IVP2#2 | 0.09 | 0.11 |
| 2-2 | IVP2#2__WPBS control 2-2 | 0.04 | −0.08 |
| | IVP1#2__IVP2#2 | −0.07 | −0.09 |

PRRS virus titers are expressed as $\log_{10}$ TCID$_{50}$/1 mL dose. Each titer value represents the mean of results obtained on two testing days with three independent titrations each testing day.

8. Discussion

The data obtained in this study demonstrated that the virus titers of IVP2 rehydrated with a standard diluent (WPBS) were all above the MID and remained stable during the four hours of incubation at room temperature. These results are consistent with the known previously determined product characteristics of IVP2 and confirm the validity of this in-use stability evaluation of the modified live PRRS virus vaccine IVP2 in associated use with IVP1.

The results obtained for both batches of IVP2 tested with either of the two batches of IVP1 at T0 show comparable virus titers to those obtained with the respective controls. The variability observed between the controls and the test samples is within the variability of the assay seen in a respective assay validation study.

The results obtained for both batches of IVP2 after reconstitution with either of the two batches of IVP1 at T2 and T4 showed stable virus titers with no to minimal ($0.12 log 10 TCID$_{50}$) decrease in titer.

9. Conclusion

The results of this study support an associated use of IVP1 and IVP2, and in-use stability of 4 hours for IVP2 when mixed with IVP1.

Example 3

A) Onset of Immunity Against PRRSV Challenge

The objective of this study was to investigate if the onset of immunity of IVP2 at 3 weeks after vaccination would be affected when used in association with IVP1. For this purpose IVP2 vaccine was reconstituted to the minimum immunizing dose (MID) with IVP1 manufactured with a high potency, wherein this combination of IVP1 and IVP2 is also named "IVP1/IVP2" in the following. This study included 52 three weeks old piglets that originated from a commercial herd in Germany. The primary parameter of the study was lung lesions at necropsy, ten to twelve days post challenge.

At inclusion none of the animals were antibody or antigen positive for PRRSV. Up to challenge with PRRSV (on day 21 post vaccination), none of the animals of the control group showed seroconversion or was tested positive for PRRSV antigen.

The animals vaccinated with IVP1/IVP2 had a median lung lesion score reduced by 52.1% as compared to the animals of the control group. Furthermore, as the IVP1/IVP2 vaccinated animals had a statistically significant higher ADWG of 164 grams per day after challenge compared to the control group, the ADWG results support the efficacy of the combination of IVP1 and IVP2.

In the animals vaccinated with IVP1/IVP2, first PRRSV antibodies were detected 14 days after vaccination (D14). While the number of PRRSV antibody positive animals did not differ statistically significant between the two groups one week after challenge, the level of antibodies was significantly higher in the vaccinated groups as compared to the control group. Ten to twelve days after challenge, all animals were positive for PRRSV antibodies and there was no statistically significant difference in the level of antibodies between the groups.

In conclusion, it was demonstrated that the onset of immunity of IVP2 at 3 weeks after vaccination was not negatively affected when used in association with IVP1.

B) Onset of Immunity Against PCV2 Challenge

The objective of this study was to evaluate the onset of immunity for IVP1 when used in association with IVP2. For this purpose IVP2 vaccine was reconstituted to target a maximum immunizing dose by adding IVP1 formulated to target a minimum potency, wherein this mixture of IVP1 and IVP2 is also named "IVP2/IVP1" hereinafter.

This study included 60 cesarean-derived, colostrum deprived (CDCD) pigs that were seronegative for PCV2, of which 30 were vaccinated with IVP2/IVP1 and 30 (the control group) received a sterile diluent (water for injection) at 3 weeks of age (i.e., on study day 0 (DO)), followed by a virulent challenge of PCV2 on D15.

Vaccination with IVP2/IVP1 resulted in a significant increase in pigs positive for PCV2 serology. Within one week post-challenge 28 pigs (93%) from the IVP2/IVP1 group sero-converted to positive levels, while 0/30 pigs (0%) from the control group were positive. Animals from the control group started to sero-convert to positive levels thirteen days post-challenge. On D21, D28, and D35 the IVP2/IVP1 group had a significantly higher proportion of pigs with positive PCV2 titers compared to the control group. By D42, the IVP2/IVP1 group was 100% serologically positive for PVC2, while the control group was 92% positive.

Upon assessment of the primary outcome parameters, the vaccination with IVP2/IVP1 significantly reduced lymphoid depletion, lymphoid inflammation and PCV2 lymphoid colonization in comparison to the control group. Furthermore, the overall level of the histologic lesions was more severe in the control group with 23/30 pigs (76.7%) having moderate to severe scores in at least one category of lymphoid lesion evaluation, whereas only 2/30 pigs (6.7%) of the vaccinated pigs had a moderate lymphoid lesion score, with none being severe.

In conclusion, IVP1 formulated at a minimum potency and used in association with IVP2 provided efficacious active immunization of 3 week old CDCD pigs when challenged with virulent PCV2 on day 15 post vaccination.

Besides, in a further vaccination-PCV2 challenge study, wherein the monovalent IVP1 was compared with a respective product which had not been subject to the downstream processing according to Example 1 (said product being named "IVP0" herein), it was seen that IVP1 was at least as efficacious as the established IVP0.

C) Duration of Immunity Against PCV2 Challenge

The objective of this study was to evaluate the duration of immunity for IVP1 when used in association with IVP2. For this purpose IVP2 vaccine was reconstituted to target a maximum immunizing dose by adding IVP1 formulated to target a minimum potency. As mentioned above (under B), this mixture of IVP1 and IVP2 is also named "IVP2/IVP1" herein.

This study included 60 cesarean-derived, colostrum deprived (CDCD) pigs that were seronegative for PCV2, of which 30 were vaccinated with IVP2/IVP1 and 30 (the control group) received a sterile diluent (water for injection) at 3 weeks of age (i.e., on study day 0 (DO)), followed by a virulent challenge of PCV2 on D119 (17 weeks duration of immunity).

As a result, the animals vaccinated with IVP2/IVP1 had a significantly reduced frequency of lymphoid depletion, lymphoid colonization, and viraemia in comparison to the control animals after PCV2 challenge. In addition, animals vaccinated with IVP2/IVP1 had a significantly reduced PCV2 viral load on all sampling days with no levels of virus considered viraemic to cause disease ((rt-PCR) test $\geq 1.0 \times 10^4$ PCV2 genomic equivalents) at any sampling point while the control animals were viraemic for a median of 28 days after challenge with PCV2. Vaccination with IVP2/IVP1 resulted in a significant increase in pigs positive for PCV2 serology from vaccination (DO) through D133 (two weeks post challenge with PCV2), which has historically been a strong indicator of efficacy. The majority of the control group (81%) were not positive for PCV2 serology until D140 (3 weeks post challenge with PCV2).

These results show that the duration of immunity of IVP1 of 17 weeks after vaccination is not negatively affected when used in association with IVP2.

D) Duration of Immunity Against PRRSV Challenge

The objective of this study is to investigate if the duration of immunity of IVP2 at 6 months after vaccination would be affected when used in association with IVP1. For this purpose, IVP2 vaccine was reconstituted to the minimum immunizing dose (MID) with IVP1 manufactured with a high potency. As mentioned above (under A), this combination of IVP1 and IVP2 is also named "IVP1/IVP2". The study includes 70 three weeks old piglets that originate from a commercial herd in Germany, wherein at inclusion none of the animals is antibody or antigen positive for PRRSV. Challenge is performed 182 days post vaccination (six months duration of immunity). The primary parameter of the study is lung lesions at necropsy, ten to twelve days post challenge.

As a result, the animals vaccinated with IVP1/IVP2 have reduced lung lesions compared to the animals of the control group after the PRRSV challenge, which shows that the duration of immunity of IVP2 of 6 months after vaccination is not negatively affected when used in association with IVP1.

Example 4

Analysis of Thiosulfate Concentration

SUMMARY

As described in Example 1, binary ethyleneimine (BEI) was used as the inactivation agent in the production of the baculovirus recombinant vaccine. Following inactivation with BEI, sodium thiosulfate is added to neutralize residual BEI.

Following inactivation of PCV2 antigen fluids with 5 mM BEI, small concentrations (typically on the order of 0.3 mM)

BEI remain detectable. The EU pharmacopeia describes that no BEI should remain in the antigen following inactivation. The EU pharmacopeia allows that the detection of residual sodium thiosulfate following inactivation is acceptable for assuring that toxic levels of BEI do not remain in the antigen. Therefore, 5 mM thiosulfate was employed for neutralizing BEI in activation steps because 5 mM BEI was initially added at the start of the inactivation step. Because a considerable amount of the BEI is consumed in reactions with nucleic acids during inactivation, and because thiosulfate and BEI react in a 1:1 stoichiometry, an excess of residual thiosulfate remains after the neutralization.

Testing thiosulfate was performed, as described below, on antigen fluids produced in accordance with Example 1.

The data from this experiment indicate that the method as described in Example 1 unexpectedly reduces thiosulfate levels below method-detectable limits already in the 10 fold concentrated and diafiltered antigen fluids.

Materials and Methods

Quantitative Determination of Sodium Thiosulfate in Antigen Fluids by High Pressure Liquid Chromatography (HPLC)

A. Reagents and Materials
  1. Sodium thiosulfate pentahydrate, reagent grade with known purity
  2. Purified Water-18 MΩcm resistivity or greater is used
  3. Acetonitrile (ACN), HPLC grade
  4. Glacial Acetic Acid, HPLC grade
  5. Tetrabutylammonium hydroxide (TBA), reagent grade
  6. HPLC column/guard-Thermo Scientific, ODS-2 Hypersil, 150×4.6 mm, 5 micron with suitable guard, ODS-2 Hypersil-2, 10×4.6 mm, 5 micron, or equivalent.
B. Solutions
  1. 20% Acetic Acid Solution
    Combine 10 mL of glacial acetic acid and 40 mL of purified water, and mix thoroughly.
  2. Eluent
    Combine 750 ml of purified water and 20 mL of TBA, and mix thoroughly. Adjust the pH of this solution to 4.5-5.0 by adding 20 ml of 20% acetic acid solution, and then combine with 250 ml of acetonitrile. Mix thoroughly and filter through a 0.2 μm nylon filter prior to use.
  3. Diluent
    Combine 800 mL of purified water and 200 mL of acetonitrile; mix thoroughly and store at ambient conditions.
C. Thiosulfate Reference Standard Solutions
  1. Sodium Thiosulfate Stock Solution (5 mM)
    Weigh 1.2 g sodium thiosulfate pentahydrate reference material and transfer into a 1000 mL Class A volumetric flask with purified water; mix thoroughly by inversion.
  2. 100% Working Standard Solution (100% WS)
    Transfer 2 mL of Sodium Thiosulfate Stock Solution into a 50 mL Class A volumetric flask. Dilute to volume with Diluent and mix thoroughly by inversion.
  3. 50% Linearity Standard Solution (50% LS)
    Transfer 1 mL of Sodium Thiosulfate Stock Solution into a 50 mL Class A volumetric flask. Dilute to volume with Diluent and mix thoroughly by inversion.

4. 150% Linearity Standard Solution (150% LS)
    Transfer 3 mL of Sodium Thiosulfate Stock Solution into a 50 mL Class A volumetric flask. Dilute to volume with Diluent and mix thoroughly by inversion.
  5. Limit of Quantitation Solution (LOQ)
    Transfer 1 mL of 50% LS into a 20 mL Class A volumetric flask. Dilute to volume with Diluent and mix thoroughly by inversion.
D. PCV2 Inactivated Antigen Fluid Test Solution
  Transfer 500 μL of inactivated antigen fluid into a 10 mL Class A volumetric flask. Dilute to volume with Diluent and mix thoroughly by inversion. Filter sample through a 0.2 μm nylon syringe filter, into an HPLC vial, wasting the first 2 to 3 mL. This is a 20 fold dilution of the antigen fluid.
E. HPLC Chromatographic Equipment and Conditions
  1. Flow rate: 1.2 mL/min
  2. Injection volume: 10 μL
  3. Column: Thermo Scientific, ODS-2 Hypersil, 150×4.6 mm, 5 micron with suitable guard, ODS-2 Hypersil-2, 10×4.6 mm, 5 micron.
  4. Temperatures: 20±2° C. sample tray temperature 25±2° C. column oven temperature
  5. Detection: 230 nm
  6. Typical Analysis Order
    Diluent for waste
    Diluent; 1 injection
    Blank; 1 injection (baseline monitoring, non-injection)
    Calibration Standards; 6 injections of 100% WS
    Linearity Standards; 2 injections each of 50, 100 and 150% solutions
    LOQ Standard; 2 injections
    Test solutions and check Standards; 2 injections per each test solution and two injections of 100% WS as check standards between a maximum of 16 sample injections and at the end of the analysis
  7. Thiosulfate retention time: about 7 minutes.
F. Calculation of Sodium Thiosulfate Content—the Content of Thiosulfate, as mM, is Calculated Using the Following Equation:

$$\text{Thiosulfate } (mM) = TS/WS \times C \times 20$$

Where: TS—Average of the thiosulfate peak areas of the two Test Solution preparation injections.
  WS—Average of the thiosulfate area response of the six 100% WS injections.
  C—Concentration of the Working Standard solution in mM (0.2 mM).
  20—Dilution factor of the test solution

Results

Several antigen fluids produced as described in Example 1 were analyzed, wherein pairs of samples were taken
  (i) after the BEI neutralization with sodium thiosulfate but before the downstream processing and
  (ii) after the downstream processing (i.e., 10 fold concentration and continuous diafiltration) but before the mixing with adjuvant and P-saline, and the concentration of sodium thiosulfate was determined.

It was found that the samples (i) taken after the BEI neutralization but before the downstream processing still had a sodium thiosulfate concentration in the millimolar range, whereas unexpectedly no sodium thiosulfate was detectable at or above the limit of detection (3 μM) in the samples (ii) taken after the downstream processing but before the mixing with adjuvant and P-saline.

Example 5

Analysis of Antigen Fluids by 2 Dimensional UPLC

A 2 dimensional UPLC method based on separation with anion exchange and size exclusion chromatography was utilized for analysis of the virus-like particle (VLP) containing antigen fluids resulting from processing as described in Example 1.

The $1^{st}$ phase of chromatography used is anion exchange chromatography, and negatively charged species are bound to the column (0-2.67 minutes in the chromatogram) and then eluted by increasing the sodium chloride concentration in the gradient.

The $2^{nd}$ phase of chromatography used is size exclusion (2.67-15 minutes in the chromatogram) where a valve is switched and an injection from the $1^{st}$ dimension of anion exchange is made onto the size exclusion column. The size exclusion column eluent mixture of the anion exchange eluents.

Materials and Methods

A. Reagents and Materials
1. 1 M Tris, pH 7.4 in water, Molecular Biology Grade
2. 5 M NaCl in water, Molecular Biology Grade
3. Purified Water—18 M MΩcm resistivity or greater is used
4. Anion Exchange Column-column volume 0.1 mL with quaternary amine functionality suitable for binding VLPs (large pore or non porous material)
5. Size exclusion column—column volume 1.75 mL with pore size of 450 Å
6. 10 N NaOH, Reagent grade
B. Solutions
1. 50 mM Tris, pH 8: Combine 50 mL of 1 M Tris, pH 7.4 with 900 mL of water. Adjust pH to 8 with 10 N NaOH, dilute to 1000 mL, and filter through a 0.22 μm filter.
2. 50 mM Tris, 2M NaCl, pH 8: Combine 50 mL of 1 M Tris, PH 7.4 and 400 mL 5 M NaCl with 300 ml of water. Adjust pH to 8 with 10 N NaOH, dilute to 1000 mL, and filter through a 0.22 μm filter.
C. PCV2 in Process Reference Solution
1. Filter antigen fluid obtained prior to inactivation through a 0.22 μm PES filter.
D. PCV2 Pre-Inactivation, or Inactivated Antigen Fluid Test Solution
1. Filter antigen fluid through a 0.22 μm PES filter.
E. 2D-UPLC Chromatographic Equipment and Conditions
1. First dimension of chromatography
a. Flow Rate: 0.6 mL/min
b. Injection Volume: 20 μL
c. System Volume: 400 μL
d. Column: 0.1 mL column volume quaternary amine column
e. Temperature: Room temperature
f. Detection: Fluorescence emission (Excitation 280 nm and emission 330 nm)
g. Gradient: A multi step gradient method of initial 100% 50 mM Tris, pH 8 at 0 minutes to 97.5% 50 mM Tris, pH 8 and 2.5% 50 mM Tris, 2 M NaCl, pH 8 at 1 minute and finally to 10% 50 mM Tris, pH 8 and 90% 50 mM Tris, 2M NaCl, pH 8 at 2 minutes is driven with a flow rate of 0.6 mL/min through the anion exchange column.
2. Second dimension of chromatography
a. Flow Rate: 0.3 mL/min
b. Injection from first dimension: 50 μL
d. Detection: Fluorescence emission (Excitation 280 nm and emission 330 nm)
e. Isocratic Gradient: 95% 50 mM Tris, pH 8: 5% 50 mM Tris, pH 8, 2M NaCl
3. Typical analysis order
a. Inject 5 2-fold serial dilutions of the PCV2 reference solution
b. Inject 1-15 samples
c. Inject 5 2-fold serial dilutions of the PCV2 reference solution
4. Switch from $1^{st}$-dimension to $2^{nd}$ dimension time: 2.67 minutes (this switching time is dependent on the system volume, which in this case is 400 μL)
5. Peak ratios listed below were calculated by integrating the peak area and taking ratios of said peak areas.

Using such 2 dimensional UPLC for analyzing VLP (ORF2) products resulting from baculovirus expression systems, different prominent peaks are seen in the resulting chromatogram:

a peak at 0-1 minutes in the chromatogram, also named "Peak A" hereinafter, representing constituents that do not bind to anion exchange columns at pH 8 (i.e. neutral or cationic constituents at pH8, e.g. positively charged proteins and/or cell culture components)

a peak at 7-8 minutes in the chromatogram, also named "Peak B" hereinafter, representing the VLP (ORF2) antigen of interest a peak at 8.5-9.5 minutes in the chromatogram, also named "Peak C" hereinafter, representing constituents ranging from the size of IgG (150 kDa) to Uracil (0.1 kDa).

It was found that 10 fold dilutions of samples taken after a downstream processing as described in Example 1 (i.e., 10 fold concentration and continuous diafiltration) showed a 99.2% decrease in peak A and a 42% decrease in peak C, in average, in comparison to upstream process samples. Further, while a decrease of peaks A and C was found, an increase of peak B was seen.

Surprisingly, the peak ratios (peak A/B and peak C/B) of the samples taken after the downstream processing as described in Example 1 were found to be only 0.3 for Peak A/B (with a Std. deviation, for 3 replicates, of 0.1) and 0.7 for Peak C/B (with a Std. deviation, for 3 replicates, of 0.2).

It was further found that in the samples taken after a downstream processing as described in Example 1 (i.e., 10 fold concentration and continuous diafiltration) there was no increase in the aggregation or the presence of larger sized species in the solution. This observation was surprising, as one would have expected, due to the dependency of aggregation on the concentration, to see on Size Exclusion Chromatography (SEC) a significant increase of larger species in such concentrated samples.

Example 6

Quantification of Free Amino Acids

A conventional method to quantitate free amino acids in insect cell culture media and spent media was applied for determining the concentration of amino acids in the antigen fluids produced as described in Example 1.

In brief, protein in the samples is precipitated with trichloracetic acid (TCA) and removed with centrifugation. The supernatant from the TCA precipitation is neutralized with sodium hydroxide and norvaline is added as an internal standard. The samples are then derivatized with o-pthaldialdehyde (OPA) and mercaptopropionic acid (MPA) in the injection loop of the UHPLC prior to being injected onto a reversed phase column for quantitation by UV absorbance at 338 nm. Based on chromatograms for a standard reference sample (external standard) the concentration of the 20 common amino acids (i.e. the 20 genetically encoded amino acids) included in the antigen fluids were determined.

Measuring the amino acid concentrations of several samples taken after the downstream processing (i.e., 10 fold concentration and continuous diafiltration) as described in Example 1 and considering the usual subsequent dilution of said samples by adding the adjuvant and P-saline, a characteristic concentration of particular amino acids in the final product (vaccine) was found/determined to be in the following range:

Tryptophane: 0.1-0.7 M;

Glutamine: 0.7-2.4 µM;

Methionine: 0.5-3.2 µM;

Arginine: 1.4-4.7 µM;

Threonine: 1.6-8.0 µM;

Lysine: 4.0-12.2 µM.

In this regard, also a typical mean concentration of said amino acids in the final product (vaccine) was determined to be in the following range:

Tryptophane: 0.2-0.6 µM;

Glutamine: 0.8-2.2 µM;

Methionine: 0.8-2.2 µM;

Arginine: 1.6-4.3 µM;

Threonine: 2.4-6.3 µM;

Lysine: 4.4-11.2 µM.

In conclusion, the results obtained from the analyses as described in Examples 4-6 show that the method as described in Example 1 provides a product which has specific inherent properties, wherein each of which may contribute to the beneficial outcome of the tests and studies as described in Examples 2 and 3.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1 provides a schematic overview of an exemplary method according to the invention.

IN THE SEQUENCE LISTING

SEQ ID NO: 1 corresponds to the sequence of a PCV2a ORF2 protein, and

SEQ ID NO: 2 corresponds to the sequence of a PCV2b ORF2 protein; "PCV2b ORF2 protein" as mentioned herein in particular relates to ORF2 protein of a so called "mutant PCV2b" which is also being considered as belonging to genotype d.

The current disclosure contains, inter alia, the following items:

1. A method of producing an immunogenic composition comprising a recombinant protein, wherein the method comprises the steps of:
   (a) providing a mixture containing
      a first liquid, and
      recombinant protein and/or quaternary structures comprising a plurality of said recombinant protein,
   (b) concentrating the recombinant protein and/or said quaternary structures in the mixture resulting from step (a) by removing a portion of the first liquid from the mixture, and
   (c) processing the solution resulting from step (b) by continuous diafiltration.

2. The method of item 1, wherein said continuous diafiltration is a continuous diafiltration against a second liquid, wherein the second liquid is different from the first liquid.

3. The method of item 1 or 2, wherein the mixture of step
   (a) additionally contains or further comprises
   a vector comprising a nucleic acid sequence encoding said recombinant protein, wherein said vector has been inactivated by an inactivating agent, and/or
   an inactivating agent, which has been neutralized by a neutralizing agent, and/or
   a neutralizing agent.

4. The method of item 3, wherein in step (c) the solution resulting from step (b) is processed by continuous diafiltration such that the concentration of the neutralized inactivating agent and/or the concentration of the neutralizing agent is decreased in the process solution.

5. A method of producing an immunogenic composition comprising a recombinant protein, in particular the method of any one items 1 to 4, wherein the method comprises the steps of:
   (a)(i) providing a mixture containing
      a first liquid,
      recombinant protein and/or quaternary structures comprising a plurality of said recombinant protein, and
      a vector comprising a nucleic acid sequence encoding said recombinant protein;
   (ii) inactivating the vector by adding an inactivating agent to the mixture of step (i);
   (iii) neutralizing the inactivating agent by adding a neutralizing agent to the mixture resulting from step (ii);
   (b) concentrating the recombinant protein and/or said quaternary structures in the mixture resulting from step (a)(iii) by removing a portion of the first liquid from the mixture, and
   (c) processing the solution resulting from step (b) by continuous diafiltration such that the concentration of the neutralized inactivating agent and/or the concentration of the neutralizing agent is decreased in the process solution.

6. The method of any one items 1 to 5, wherein in step (b) the removing of a portion of the first liquid from said mixture consists of or comprises filtering said mixture with at least one filter, wherein said at least one filter preferably comprises a filter membrane.

7. The method of any one of items 3 to 6, wherein in step (b) said concentrating comprises
   feeding the mixture into a filter system containing at least one filter, wherein the at least one filter comprises a filter membrane having a membrane pore size allowing the neutralized inactivating agent and/ or the neutralizing agent to pass through while retaining the recombinant protein and/or said quaternary structures in the bulk flow, discharging the permeate comprising the neutralized inactivating agent and/or the neutralizing agent.

8. The method of any one of items 3 to 7, wherein in step (c) said continuous diafiltration comprises feeding the solution into a filter system containing at least one filter, wherein the at least one filter comprises a filter membrane having a membrane pore size allowing the neutralized inactivating agent and/or the neutralizing agent to pass through while retaining the recombinant protein and/or said quaternary structures in the bulk flow, discharging the permeate comprising the neutralized inactivating agent and/or the neutralizing agent, adding a second liquid to the bulk flow at a rate equal to the permeate flow, wherein the second liquid is different from the first liquid.

9. The method of any one of items 6 to 8, wherein the at least one filter is at least one flat sheet filter and/or at least one hollow fiber filter, and wherein the at least one flat sheet filter is preferably at least one cassette filter.

10. The method of any one of items 6 to 9, wherein the at least one filter are 2-8 filters, preferably 5-7 filters, and/or wherein each of the at least one filter has a total filter area of about 16-26 m², preferably of about 20-22 m².

11. The method of any one of items 6 to 10, wherein the filter membrane has an average pore size that is smaller than the recombinant protein and/or said quaternary structures, and/or wherein the filter membrane has a molecular weight cut off of between about 200 kDa and about 500 kDa.

12. The method of any one of items 6 to 11, wherein the filter membrane consists of or comprises a material selected from the group consisting of polyethersulfone, cellulose hydrate, regenerated cellulose, stabilized cellulose, cross-linked cellulose, cross-linked cellulose hydrate, cellulose acetate, polyamide, polyurethane, polypropylene, polysulfone, polycarbonate, nylon, polyimide, and combinations thereof, and/or wherein the filter membrane preferably consists of or comprises polyethersulfone, or wherein the filter membrane is optionally a stabilized cellulose based membrane.

13. The method of any one of items 7 to 12, wherein in step (b) and in step (c) the same filter system is utilized.

14. The method of any one of items 5 to 13, wherein step (iii) is carried out in a first container, and wherein the mixture resulting from neutralizing the inactivating agent is transferred from the first container to a second container connected with a filter system, and wherein after transferring the mixture from the first to the second container a valve between the first container and the second container is closed, and the empty first container is filled with the second liquid, in step (b) the mixture is circulated through the second container and the filter system until the concentrating is completed, and in step (c) the valve between the first and the second container is opened and the second liquid is continuously led from the first container to the second container while the mixture is circulated through the filter system and the second container.

15. The method of any one of items 1 to 14, wherein said first liquid comprises a portion of cell culture medium or consists of cell culture medium, and wherein the cell culture medium is preferably insect cell culture medium.

16. The method of any one of items 1 to 15, wherein the volume of the mixture resulting from step (a) is from 1000 L to 10000 L, preferably from 2000 L to 8000 L, and most preferably from 3000 L to 5000 L.

17. The method of any one of items 1 to 15, wherein in step (b) said recombinant protein and/or said quaternary structures is finally concentrated at least 5×, preferably at least 8×, more preferably 9× to 11×, in comparison to the volume of the mixture resulting from step (a).

18. The method of any one of items 2 to 17, wherein the second liquid is a buffer solution, preferably P-Saline or phosphate buffered saline (PBS).

19. The method of any one of items 8 to 18, wherein in step (c) the total volume of the second liquid added to the bulk flow is at least 5×, preferably at least 7×, more preferably at least 9×, the volume of the solution resulting from step (b), and/or wherein the total volume of the second liquid added to the bulk flow is most preferably about the volume of the mixture resulting from step (a).

20. The method of any one of items 1 to 19, wherein said method further comprises the step of (d) admixing the mixture remaining after step (c) with a further component selected from the group consisting of pharmaceutically acceptable carriers, adjuvants, diluents, excipients, and combinations thereof, and wherein the concentration of the recombinant protein and/or the concentration of said quarternary structures in the solution resulting from said admixing is preferably about the concentration of the recombinant protein and/or said quaternary structures in the mixture resulting from step (a).

21. The method of any one items 1 to 20, wherein the mixture used for step (a) is obtainable by a procedure comprising the steps of (1) permitting infection of susceptible cells in culture with a vector comprising a nucleic acid sequence encoding said recombinant protein, wherein said recombinant protein is expressed by said vector, (2) thereafter recovering the recombinant protein and/or quaternary structures comprising a plurality of said recombinant protein from the cell culture, wherein preferably cell debris is separated from the recombinant protein and/or said quaternary structures via a separation step, preferably including a micro filtration through at least one filter, preferably two filters, wherein the at least one filter preferably has a pore size larger than the recombinant protein and/or quaternary structures containing a plurality of said recombinant protein, in particular has a pore size of about 1 to about 20 μm and/or about 0.1 μm to about 4 μm.

22. The method of item 21, wherein the separation step includes or consists of:

a micro filtration through one or more filters having a pore size of about 2 μm to about 15 μm, and/or a micro filtration through one or more filters having a pore size of about 0.8 μm to about 1.0 μm.

23. The method of item 21 or 22, wherein the cell culture in step (1) is maintained at 22-32° C., preferably while the recombinant protein is expressed by said vector, and/or wherein the recovering in step (2) occurs 5 to 8 days, preferably 8 days, after inoculation of the cells with the vector.

24. The method of any one of items 1 to 23, wherein said recombinant protein is a PCV2 ORF2 protein preferably comprising or consisting of a sequence having at least at least 90%, at least 91%, at least 92%, at least 93%, at least 94%, at least 95%, at least 96%, at least 97%, at least 98%, at least 99%, at least 99.1%, at least 99.5%, or 100% sequence identity with the sequence of SEQ ID NO:1 and/or SEQ ID NO:2.

25. The method of any one of items 1 to 24, wherein the quaternary structures are virus-like particles.

26. The method of any one of items 3 to 25, wherein the vector is a recombinant virus, preferably baculovirus, and/or wherein the nucleic acid sequence is a DNA sequence.

27. The method of any one of items 3 to 26, wherein the inactivating agent is an aziridine compound, preferably binary ethylenimine (BEI), and/or wherein the inactivating agent is added in a molar excess in relation to the vector.

28. The method of any one of items 3 to 27, wherein the neutralizing agent is sodium thiosulfate and/or wherein the neutralizing agent is added in a molar excess in relation to the inactivating agent.

29. The method of any one of items 5 to 28, wherein in step (iii) the neutralizing agent is added in equivalent amount as compared to the amount of inactivating agent added in step (ii).

30. The method of any one of items 5 to 29, wherein the mixture remaining after step (c) comprises a concentration of the inactivating agent which is less than one thousands of the concentration of the neutralizing agent resulting from step (iii).

31. The method according to any one of items 1 to 30, wherein the virucidal activity of the immunogenic composition resulting from said method is reduced by at least 20% as compared to an immunogenic composition mixture that has not undergone the concentrating of step (b) and the continuous diafiltration of step (c) of said method, and/or wherein the immunogenic composition produced by said method causes a loss of less than 1 log $TCID_{50}$ per mL of a live virus, preferably of less than 0.7 log $TCID_{50}$ per mL of a live virus, when the live virus is mixed with the immunogenic composition for four or more hours, in particular at room temperature.

32. The method according to any one of items 1 to 31, wherein the method further comprises the step of combining the mixture remaining after step (c) and/or step (d) with at least one additional antigen.

33. The method according to item 31 or 32, wherein the live virus or the at least one additional antigen is Porcine Reproductive and Respiratory Syndrome (PRRS) virus.

34. An immunogenic composition obtainable by a method according to any one of items 1 to 33.

35. The immunogenic composition of item 34, wherein the immunogenic composition is obtainable by a method according to any one of items 28 to 33, and wherein the mixture remaining after step (c) comprises less than 3 μM sodium thiosulfate.

36. The immunogenic composition of item 34, wherein the immunogenic composition is obtainable by a method according to any one of items 28 to 33, and wherein the immunogenic composition resulting from step (d) is substantially free from sodium thiosulfate.

37. An immunogenic composition, in particular the immunogenic composition of any one of items 34 to 36, comprising a recombinant PCV2 ORF2 protein preferably comprising or consisting of a sequence having at least 90%, at least 91%, at least 92%, at least 93%, at least 94%, at least 95%, at least 96%, at least 97%, at least 98%, at least 99%, at least 99.1%, at least 99.5%, or 100% sequence identity with the sequence of SEQ ID NO:1 and/or SEQ ID NO: 2, and 1-10 μM L-arginine and/or 1-10 μM L-lysine, and wherein preferably the immunogenic composition is substantially free from a neutralized inactivating agent and/or substantially free from a neutralizing agent.

38. An immunogenic composition, in particular the immunogenic composition of any one of items 34 to 37, preferably obtainable by any such method comprising step (d), wherein the immunogenic composition comprises a recombinant PCV2 ORF2 protein preferably comprising or consisting of a sequence having at least 90%, at least 91%, at least 92%, at least 93%, at least 94%, at least 95%, at least 96%, at least 97%, at least 98%, at least 99%, at least 99.1%, at least 99.5%, or 100% sequence identity with the sequence of SEQ ID NO:1 and/or SEQ ID NO: 2, and 0.1-1 μM L-Tryptophane; and/or
0.1-3 μM L-Glutamine; and/or
0.2-4 μM L-Methionine; and/or
1-10 μM L-Arginine; and/or
1-10 μM L-Threonine; and/or
1-15 μM L-Lysine.

39. The immunogenic composition of any one of items 34 to 38, wherein said immunogenic composition comprises 0.1-0.7 μM L-Tryptophane; and/or
0.7-2.4 μM L-Glutamine; and/or
0.5-3.2 μM L-Methionine; and/or
1.4-4.7 μM L-Arginine; and/or
1.6-8.0 μM L-Threonine; and/or
4.0-12.2 μM L-Lysine.

40. The immunogenic composition of item 39, wherein said immunogenic composition comprises 0.2-0.6 μM L-Tryptophane; and/or
0.8-2.2 μM L-Glutamine; and/or
0.8-2.2 μM L-Methionine; and/or
1.6-4.3 μM L-Arginine; and/or
2.4-6.3 μM L-Threonine; and/or
4.4-11.2 μM L-Lysine.

41. The immunogenic composition of any one of items 34 to 40, wherein said composition comprises 0.7-2.4 μM L-Glutamine and 4.0-12.2 μM L-Lysine.

42. The immunogenic composition of any one of items 34 to 41, wherein said composition comprises 0.8-2.2 μM L-Glutamine and 4.4-11.2 μM L-Lysine.

43. An immunogenic composition, in particular the immunogenic composition of any one of items 34 to 42, preferably obtainable by any such method comprising step (d), wherein the immunogenic composition when subjected to a 2 dimensional (2 D) Ultra Performance Liquid Chromatography (UPLC) at room temperature exhibits a ratio of the peak A area to the peak B area of 0.2-0.4 and/or a ratio of the peak C area to the peak B area of 0.5-0.9, wherein the 2 D UPLC comprises a first dimension of chromatography with a system volume of 400 μL, wherein a sample comprising the immunogenic composition is injected into an anion exchange column with 0.1 mL column volume packed with quarternary amine-functionalized material suitable for binding virus like-particles, and a multi-step gradient method of initial 100% 50 mM Tris, pH 8 at 0 minutes to 97.5% 50 mM Tris, pH 8 and 2.5% 50 mM Tris, 2 M NaCl, pH 8 at 1 minute and finally to 10% 50 mM Tris, pH 8 and 90% 50 mM Tris, 2M NaCl, pH 8 at 2 minutes is driven with a flow rate of 0.6 mL/min through the anion exchange column, and wherein at the retention time of 2.67 min it is switched from the first dimension of chromatography to a second dimension of chromatography, wherein 50 μL eluate of the first dimension of chromatography are driven with a flow rate of 0.3 mL/min through a size exclusion column with a 1.75 mL column volume with a pore size of 450 Å, and wherein a chromatogram is recorded by monitoring the fluorescence emission at the wavelength of 330 nm and an excitation wavelength of 280 nm, and wherein the peak A area is the peak area of the highest peak at the retention time of 0-1 minutes in the chromatogram;

the peak B area is the peak area of the highest peak at the retention time of 7-8 minutes in the chromatogram;

the peak C area is the peak area of the highest peak at the retention time of 8.5-9.5 minutes in the chromatogram.

44. The immunogenic composition of any one of items 34 to 43, wherein said immunogenic composition is substantially free from a neutralizing agent, preferably substantially free from sodium thiosulfate.

45. The immunogenic composition according to item any one of items 34 to 44, wherein the immunogenic composition further comprises an attenuated live virus, preferably an attenuated Porcine Reproductive and Respiratory Syndrome (PRRS) virus, or an attenuated live bacterium.

46. The immunogenic composition according to any one of items 34 to 45, wherein the immunogenic composition induces a protective immune response against the pathogen from which the amino acid sequence of the recombinant protein is derived, preferably against PCV2, after the administration of one dose of the immunogenic composition.

47. The immunogenic composition according to any one of items 45 or 46, wherein the immunogenic composition induces a protective immune response against PRRS virus after the administration of one dose of the immunogenic composition.

48. Kit comprising a container containing the immunogenic composition according to any one of items 34 to 47.

49. Kit comprising a container containing the immunogenic composition produced by the method according to any one according to any one of items 1 to 33.

50. The kit according to item 48 or 49 further comprising at least one additional container containing at least one additional antigen selected from the group consisting of attenuated live virus, preferably attenuated PRRS virus, and attenuated live bacterium.

51. The immunogenic composition according to any one of items 34 to 50 and/or the kit according to any one of items 48 to 50, further comprising one or more attenuated or inactivated non-PRRSV pathogens or antigenic material thereof.

52. The immunogenic composition according to any one of items 34 to 47 and 51 and/or the kit according to any one of items 48 to 50 for use as a medicament, preferably as a vaccine.

53. The immunogenic composition according to any one of items 34 to 47 and 51 to 52 and/or the kit according to any one of items 48 to 52, for use in a method of inducing a protective immune response against at least one pathogen and/or reducing one or more clinical signs of at least one pathogen infection in an animal, wherein the at least one pathogen is preferably selected from the group consisting of PCV2, PRRSV, non-PRRSV pathogens, and combinations thereof.

54. The immunogenic composition and/or the kit according to item 51, in particular for the use according to item 52 or 53, wherein said non-PRRSV pathogens are selected from *Mycoplasma hyopneumoniae*, Pseudorabies virus, Porcine influenza virus, Porcine parvovirus, Transmissible gastroenteritis virus, *Escherichia coli, Erysipelothrix rhusiopathiae, Bordetella bronchiseptica, Salmonella cholerasuis, Haemophilus parasuis, Pasteurella multocida, Streptococcus suis* and *Actinobacillus pleuropneumoniae*.

55. A method of producing an immunogenic composition comprising a recombinant protein, wherein the method comprises the steps of:

(a) providing a mixture containing a first liquid, and recombinant PCV2 ORF2 protein and/or virus-like particles comprising a plurality of a recombinant PCV2 ORF2 protein, (b) forming a bulk flow solution by concentrating the recombinant PCV2 ORF2 protein and/or said virus-like particles in the mixture resulting from step (a) by removing a portion of the first liquid from the mixture, and (c) forming a process solution by processing the bulk flow solution resulting from step (b) by continuous diafiltration.

56. The method of item 55, wherein the mixture of step (a) additionally contains or further comprises a vector comprising a nucleic acid sequence encoding said recombinant PCV2 ORF2 protein, wherein said vector has been inactivated by an inactivating agent, and/or an inactivating agent, which has been neutralized by a neutralizing agent, and/or a neutralizing agent, and/or wherein in step (c) the bulk flow solution resulting from step (b) is processed by continuous diafiltration such that the concentration of the neutralized inactivating agent and/or the concentration of the neutralizing agent is decreased in the process solution.

57. The method of item 55 or 56, wherein the method comprises the steps of:

(a)(i) providing a mixture containing a first liquid, recombinant PCV2 ORF2 protein and/or virus-like particles comprising a plurality of a recombinant PCV2 ORF2 protein, and a vector comprising a nucleic acid sequence encoding said recombinant protein;

(ii) inactivating the vector by adding an inactivating agent to the mixture of step (i);

(iii) neutralizing the inactivating agent by adding a neutralizing agent to the mixture resulting from step (ii);

(b) forming a bulk flow solution by concentrating the recombinant PCV2 ORF2 protein and/or said virus-like particles in the mixture resulting from step (a)(iii) by removing a portion of the first liquid from the mixture, and (c) forming a process solution by processing the bulk flow solution resulting from step (b) by continuous diafiltration such that the concentration of the neutralized inactivating agent and/or the concentration of the neutralizing agent is decreased in the process solution.

58. The method of any one of items 55 to 57, wherein in step (b) the removing of a portion of the first liquid from said mixture consists of or comprises filtering said mixture with at least one filter, wherein said at least one filter preferably comprises a filter membrane.

59. The method of any one of items 55 to 58, wherein the mixture of step (a) is concentrated by:

forming a permeate by feeding the mixture into a filter system containing at least one filter, wherein the at least one filter comprises a filter membrane having a membrane pore size allowing the neutralized inactivating agent and/or the neutralizing agent to pass through while retaining the recombinant PCV2 ORF2 protein and/or said virus-like particles in the bulk flow solution, wherein the permeate comprising the neutralized inactivating agent and/or the neutralizing agent, discharging the permeate, and/or wherein said continuous diafiltration of step (c) comprises:

forming a permeate by feeding the bulk flow solution of step (b) into a filter system containing at least one filter, wherein the at least one filter comprises a filter membrane having a membrane pore size allowing the neutralized inactivating agent and/or the neutralizing agent to pass through while retaining the recombinant PCV2 ORF2 protein and/or said virus-like particles in the bulk flow solution, wherein the permeate comprising the neutralized inactivating agent and/or the neutralizing agent, discharging the permeate, and adding a second liquid to the bulk flow solution at a rate equal to the rate the permeate is discharged, wherein the second liquid is different from the first liquid.

60. The method of item 58 or 59, wherein the at least one filter is at least one flat sheet filter and/or at least one hollow fiber filter, and wherein the at least one flat sheet filter is preferably at least one cassette filter, and/or wherein the at least one filter are 2-8 filters, preferably 5-7 filters, and/or wherein each of the at least one filter has a total filter area of about 16-26 m$^2$, preferably of about 20-22 m$^2$, and/or wherein the filter membrane has an average pore size that is smaller than the recombinant PCV2 ORF2 protein and/or said virus-like particles, and/or wherein the filter membrane has a molecular weight cut off of between about 200 kDa and about 500 kDa, and/or wherein the filter membrane consists of or comprises a material selected from the group consisting of polyethersulfone, cellulose hydrate, regenerated cellulose, stabilized cellulose, cross-linked cellulose, cross-linked cellulose hydrate, cellulose acetate, polyamide, polyurethane, polypropylene, polysulfone, polycarbonate, nylon, polyimide, and combinations thereof, and/or wherein the filter membrane preferably consists of or comprises polyethersulfone, or wherein the filter membrane is optionally a stabilized cellulose based membrane.

61. The method of item 59 or 60, wherein the same filter system is utilized in step (b) and in step (c).

62. The method of any one of items 57 to 61, wherein step (iii) is carried out in a first container, and wherein the mixture of step (a) resulting from neutralizing the inactivating agent is transferred from the first container to a second container connected with a filter system, and wherein after transferring the mixture of step (a) from the first to the second container, a valve between the first container and the second container is closed, and the empty first container is filled with the second liquid, in step (b) the mixture of step (a) is circulated through the second container and the filter system until the mixture of step (a) is concentrated, thereby forming the bulk flow solution of step (b); and in step (c) the valve between the first and the second container is opened and the second liquid is continuously led from the first container to the second container while the bulk flow solution is circulated through the filter system and the second container until the process solution is formed.

63. The method of any one of items 55 to 62, wherein said first liquid comprises a portion of a cell culture medium or consists of a cell culture medium, and wherein the cell culture medium is preferably insect cell culture medium, and/or wherein the mixture resulting from step (a) has a volume, wherein the volume of the mixture is from 1000 L to 10000 L, preferably from 2000 L to 8000 L, and most preferably from 3000 L to 5000 L, and/or wherein in step (b) the mixture of step (a) is concentrated into the bulk flow solution, until the recombinant PCV2 ORF2 protein and/or the virus-like particles of the bulk flow solution are at least 5×, preferably at least 8×, more preferably 9× to 11× concentrated, in comparison to the concentration of the recombinant PCV2 ORF2 protein and/or the virus-like particles in the volume of the mixture resulting from step (a).

64. The method of any one of items 59 to 63, wherein the second liquid is a buffer solution, preferably P-Saline or phosphate buffered saline (PBS), and/or wherein in step (c) the total volume of the second liquid added to the bulk flow solution is at least 5×, preferably at least 7×, more preferably at least 9×, the volume of the bulk flow solution resulting from step (b), and/or wherein the total volume of the second liquid added to the bulk flow solution is most preferably about the volume of the mixture resulting from step (a) that was concentrated.

65. The method of any one of items 55 to 64, wherein said method further comprises the step of
   (d) forming a solution D by admixing the process solution remaining after step (c) with a further component selected from the group consisting of pharmaceutically acceptable carriers, adjuvants, diluents, excipients, and combinations thereof, and wherein the concentration of the recombinant PCV2 ORF2 protein and/or the concentration of said virus-like particles in the solution D resulting from said admixing is preferably about the concentration of the PCV2 ORF2 recombinant protein and/or said virus-like particles in the mixture resulting from step (a).

66. The method of any one of items 55 to 65, wherein said recombinant PCV2 ORF2 protein comprises or consists of a sequence having at least at least 90%, at least 91%, at least 92%, at least 93%, at least 94%, at least 95%, at least 96%, at least 97%, at least 98%, at least 99%, at least 99.1%, at least 99.5%, or 100% sequence identity with the sequence of SEQ ID NO:1 and/or SEQ ID NO:2.

67. The method of any one of items 56 to 66, wherein the vector is a recombinant virus, preferably baculovirus, and/or wherein the nucleic acid sequence is a DNA sequence,
   and/or wherein the inactivating agent is an aziridine compound, preferably binary ethylenimine (BEI), and/or wherein the inactivating agent is added in a molar excess in relation to the vector,
   and/or wherein the neutralizing agent is sodium thiosulfate and/or wherein the neutralizing agent is added in a molar excess in relation to the inactivating agent.

68. The method according to any one of items 55 to 67, wherein the immunogenic composition in solution D has a virucidal activity, and the virucidal activity of the immunogenic composition resulting from said method is reduced by at least 20% as compared to the immunogenic composition not produced by the concentrating of step (b) and the continuous diafiltration of step (c) of said method, and/or wherein the immunogenic composition produced by said method causes a loss of less than 1 log $TCID_{50}$ per mL of a live virus, preferably of less than 0.7 log $TCID_{50}$ per mL of a live virus, when the live virus is mixed with the immunogenic composition for four or more hours.

69. The method of item 68 wherein the live virus is mixed with the immunogenic composition for four or more hours at room temperature.

70. The method according to any one of items 55 to 69, wherein the method further comprises the step of combining the processing solution remaining after step (c) and/or the solution D remaining after step (d) with at least one additional antigen,
   and/or wherein the at least one additional antigen is preferably Porcine Reproductive and Respiratory Syndrome (PRRS) virus.

71. An immunogenic composition produced by the method according to any one of items 55 to 70.

72. The immunogenic composition of item 71, comprising a recombinant PCV2 ORF2 protein preferably comprising or consisting of a sequence having at least 90%, at least 91%, at least 92%, at least 93%, at least 94%, at least 95%, at least 96%, at least 97%, at least 98%, at least 99%, at least 99.1%, at least 99.5%, or 100% sequence identity with the sequence of SEQ ID NO:1 and/or SEQ ID NO: 2, and
   1-10 µM L-arginine and/or 1-10 µM L-lysine and wherein preferably the immunogenic composition is substantially free from the neutralized inactivating agent and/or substantially free from the neutralizing agent.

73. The immunogenic composition according to item 71 or 72, wherein the immunogenic composition further comprises an attenuated live virus, preferably an attenuated Porcine Reproductive and Respiratory Syndrome (PRRS) virus, or an attenuated live bacterium,
   and/or wherein the immunogenic composition induces a protective immune response against PCV2, after the administration of one dose of the immunogenic composition,
   and/or wherein the immunogenic composition induces a protective immune response against PRRS virus after the administration of one dose of the immunogenic composition.

74. A kit comprising a container containing the immunogenic composition according to any one of items 71 to 73, and wherein the kit preferably
   comprises at least one additional container containing at least one additional antigen selected from the group consisting of attenuated live virus, preferably attenuated PRRS virus, and attenuated live bacterium.

75. The immunogenic composition according to any one of items 71 to 73 and/or the kit according to item 74 for use as a medicament, preferably as a vaccine.

76. The immunogenic composition according to any one of items 71 to 73 and 75 and/or the kit according to item 74 or 75, for use in a method of
   inducing a protective immune response against at least one pathogen and/or
   reducing one or more clinical signs of at least one pathogen infection
in an animal, wherein the at least one pathogen is preferably selected from the group consisting of PCV2, PRRSV, non-PRRSV pathogens, and combinations thereof.

---

The invention claimed is:

1. A method of producing an immunogenic composition comprising a recombinant Porcine circovirus type 2 (PCV2) ORF2 protein, wherein the method comprises the steps of:
(a)(i) providing a mixture containing
a first liquid,
recombinant PCV2 ORF2 protein and/or virus-like particles comprising a plurality of a recombinant PCV2 ORF2 protein, and
a vector comprising a nucleic acid sequence encoding said recombinant
PCV2 ORF2 protein;
(ii) inactivating the vector by adding an inactivating agent to the mixture of step (i);
(iii) neutralizing the inactivating agent by adding a neutralizing agent to the mixture resulting from step (ii);
(b) concentrating the recombinant PCV2 ORF2 protein and/or said virus-like particles in the mixture resulting from step (a) (iii) by removing a portion of the first liquid from the mixture, and
(c) processing the solution resulting from step (b) by continuous diafiltration such that the concentration of the neutralized inactivating agent and the concentration of the neutralizing agent is decreased in the process solution.

2. The method of claim 1, wherein in step (b) the removing of a portion of the first liquid from said mixture consists of or comprises filtering said mixture with at least one filter.

3. The method of claim 2, wherein the at least one filter is at least one flat sheet filter or at least one hollow fiber filter.

4. The method of claim 1, wherein in step (b) said concentrating comprises
feeding the mixture into a filter system containing at least one filter, wherein the at least one filter comprises a filter membrane having a membrane pore size allowing the neutralized inactivating agent and/or the neutralizing agent to pass through while retaining the recombinant PCV2 ORF2 protein and/or said virus-like particles in the bulk flow, and
discharging the permeate comprising the neutralized inactivating agent and the neutralizing agent, wherein a second liquid is not added to the bulk flow.

5. The method of claim 1, wherein said first liquid comprises a portion of cell culture medium or consists of cell culture medium.

6. The method of claim 1, wherein said method further comprises the step of
(d) admixing the mixture remaining after step (c) with a further component selected from the group consisting of pharmaceutically acceptable carriers, adjuvants, diluents, excipients, and combinations thereof.

7. The method according to claim 6, wherein the method further comprises the step of combining the mixture remaining after step (c) or step (d) with at least one additional antigen,
and wherein the at least one additional antigen is an attenuated live Porcine Reproductive and Respiratory Syndrome (PRRS) virus.

8. The method of claim 1, wherein said recombinant PCV2 ORF2 protein comprises a sequence having at least at least 90%, at least 91%, at least 92%, at least 93%, at least 94%, at least 95%, at least 96%, at least 97%, at least 98%, at least 99%, at least 99.1%, at least 99.5%, or 100% sequence identity with the sequence of SEQ ID NO: 1 or SEQ ID NO:2.

9. The method of claim 1, wherein the vector is a recombinant virus.

10. The method according to claim 1, wherein the virucidal activity of the immunogenic composition resulting from said method is reduced by at least 20% as compared to an immunogenic composition mixture that has not undergone the concentrating of step (b) and the continuous diafiltration of step (c) of said method.

11. The method according to claim 1, wherein the method further comprises the step of combining the mixture remaining after step (c) or step (d) with at least one additional antigen,
and wherein the at least one additional antigen is Porcine Reproductive and Respiratory Syndrome (PRRS) virus.

12. The method of claim 1, wherein said continuous diafiltration further comprises:
feeding the solution into a filter system containing at least one filter, wherein the at least one filter comprises a filter membrane having a membrane pore size allowing the neutralized inactivating agent and the neutralizing agent to pass through while retaining the recombinant PCV2 ORF2 protein and/or said virus-like particles in the bulk flow,
discharging the permeate comprising the neutralized inactivating agent and the neutralizing agent,
adding a second liquid to the bulk flow at a rate equal to the permeate flow, wherein the second liquid is different from the first liquid.

13. The method of claim 12, wherein in step (b) and in step (c) the same filter system is utilized.

14. The method of claim 12, wherein step (iii) is carried out in a first container, and wherein the mixture resulting from neutralizing the inactivating agent is transferred from the first container to a second container connected with a filter system, and wherein after transferring the mixture from the first to the second container a valve between the first container and the second container is closed, and the empty first container is filled with the second liquid, in step (b) the mixture is circulated through the second container and the filter system until the concentrating is completed, and in step (c) the valve between the first and the second container is opened and the second liquid is continuously led from the first container to the second container while the mixture is circulated through the filter system and the second container.

15. The method of claim 12, wherein the second liquid is a P-Saline or phosphate buffered saline (PBS) buffer solution, and wherein when said P-saline is the buffer solution, the P-saline comprises 0.8-0.9% (w/v) NaCl dissolved in water and pH adjusted to 6.8-7.0.

16. An immunogenic composition, comprising a recombinant PCV2 ORF2 protein comprising a sequence having at least 90%, at least 91%, at least 92%, at least 93%, at least 94%, at least 95%, at least 96%, at least 97%, at least 98%, at least 99%, at least 99.1%, at least 99.5%, or 100% sequence identity with the sequence of SEQ ID NO: 1 or SEQ ID NO:2, and 1-10 µM L-arginine and wherein the immunogenic composition is substantially free from a neutralized inactivating agent and/or substantially free from a neutralizing agent.

17. The immunogenic composition according to claim 16 comprising 4.0-12.2 µM L-lysine.

18. The immunogenic composition according to claim 16, wherein said immunogenic composition is produced by a method comprising the steps of:

(a) (i) providing a mixture containing a first liquid, recombinant PCV2 ORF2 protein and/or virus-like particles comprising a plurality of a recombinant PCV2 ORF2 protein, and a vector comprising a nucleic acid sequence encoding said recombinant PCV2 ORF2 protein;

(ii) inactivating the vector by adding an inactivating agent to the mixture of step (i);

(iii) neutralizing the inactivating agent by adding a neutralizing agent to the mixture resulting from step (ii);

(b) concentrating the recombinant PCV2 ORF2 protein and/or said virus-like particles in the mixture resulting from step (a) (iii) by removing a portion of the first liquid from the mixture, and (c) processing the solution resulting from step (b) by continuous diafiltration such that the concentration of the neutralized inactivating agent and the concentration of the neutralizing agent is decreased in the process solution.

19. The immunogenic composition according to claim 16, wherein the immunogenic composition further comprises an attenuated live Porcine Reproductive and Respiratory Syndrome (PRRS) virus, or an attenuated live bacterium.

20. A kit comprising a container containing the immunogenic composition according to claim 16.

21. The kit according to claim 20, wherein the kit comprises at least one additional container containing at least one additional antigen selected from the group consisting of attenuated live PRRS virus and attenuated live bacterium.

22. The immunogenic composition according to claim 16 or the kit according to claim 21, for use in a method of inducing a protective immune response against PCV2 or reducing one or more clinical signs of PCV2 infection in an animal.

23. The immunogenic composition according to claim 16 or the kit according to claim 21, for use in a method of inducing a protective immune response against at least one pathogen or reducing one or more clinical signs of at least one pathogen infection in an animal, wherein the at least one pathogen is selected from the group consisting of PCV2, attenuated live PRRSV, and a combination thereof.

\* \* \* \* \*

SEQUENCE LISTING

```
Sequence total quantity: 2
SEQ ID NO: 1          moltype = AA  length = 233
FEATURE               Location/Qualifiers
source                1..233
                      mol_type = protein
                      organism = unidentified
                      note = Porcine circovirus
SEQUENCE: 1
```

```
MTYPRRRYRR RRHRPRSHLG QILRRRPWLV HPRHRYRWRR KNGIFNTRLS RTFGYTVKAT  60
TVTTPSWAVD MMRFNIDDFV PPGGGTNKIS IPFEYYRIRK VKVEFWPCSP ITQGDRGVGS  120
TAVILDDNFV TKATALTYDP YVNYSSRHTI PQPFSYHSRY FTPKPVLDST IDYFQPNNKR  180
NQLWLRLQTS RNVDHVGLGT AFENSKYDQD YNIRVTMYVQ FREFNLKDPP LEP         233

SEQ ID NO: 2            moltype = AA  length = 234
FEATURE                Location/Qualifiers
source                 1..234
                       mol_type = protein
                       organism = unidentified
                       note = Porcine circovirus
SEQUENCE: 2
MTYPRRRFRR RRHRPRSHLG QILRRRPWLV HPRHRYRWRR KNGIFNTRLS RTIGYTVKKT  60
TVRTPSWNVD MMRFNINDFL PPGGGSNPLT VPFEYYRIRK VKVEFWPCSP ITQGDRGVGS  120
TAVILDDNFV TKANALTYDP YVNYSSRHTI TQPFSYHSRY FTPKPVLDRT IDYFQPNNKR  180
NQLWLRLQTT GNVDHVGLGT AFENSIYDQD YNIRITMYVQ FREFNLKDPP LNPK        234
```